United States Patent
Uehira et al.

(10) Patent No.: US 9,533,945 B2
(45) Date of Patent: Jan. 3, 2017

(54) KETENE IMINE COMPOUND, POLYESTER FILM, BACK SHEET FOR SOLAR CELL MODULE AND SOLAR CELL MODULE

(71) Applicant: FUJIFILM Corporation, Tokyo (JP)

(72) Inventors: Shigeki Uehira, Shizuoka (JP); Makoto Fukuda, Shizuoka (JP); Michihiro Ogawa, Shizuoka (JP); Masaomi Makino, Shizuoka (JP); Masatoshi Mizumura, Shizuoka (JP); Seiya Sakurai, Shizuoka (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/704,531

(22) Filed: May 5, 2015

(65) Prior Publication Data

US 2015/0232419 A1    Aug. 20, 2015

Related U.S. Application Data

(63) Continuation of application No. PCT/JP2013/079840, filed on Nov. 5, 2013.

(30) Foreign Application Priority Data

Nov. 6, 2012 (JP) ................................. 2012-244742
Nov. 1, 2013 (JP) ................................. 2013-228466

(51) Int. Cl.
C07C 251/16 (2006.01)
C08G 63/91 (2006.01)
H01L 31/049 (2014.01)
C08J 5/18 (2006.01)

(52) U.S. Cl.
CPC ........... C07C 251/16 (2013.01); C08G 63/916 (2013.01); C08J 5/18 (2013.01); H01L 31/049 (2014.12); C08J 2367/03 (2013.01)

(58) Field of Classification Search
CPC ........ C07C 251/16; C08G 63/916; C08J 5/18; C08J 2367/03; H01L 31/049
See application file for complete search history.

(56) References Cited

U.S. PATENT DOCUMENTS

| | | | |
|---|---|---|---|
| 3,692,745 A | 9/1972 | Molenaar | |
| 5,763,538 A * | 6/1998 | Hunter | C08K 5/1515 525/437 |
| 6,200,659 B1 | 3/2001 | Fujimori et al. | |
| 6,365,659 B1 | 4/2002 | Aoyama et al. | |
| 6,500,506 B1 | 12/2002 | Suzuki et al. | |
| 6,500,915 B1 | 12/2002 | Fujimori et al. | |
| 6,590,044 B2 | 7/2003 | Suzuki et al. | |
| 7,138,481 B2 | 11/2006 | Matsumoto | |
| 7,544,762 B2 | 6/2009 | Yamamoto et al. | |
| 2003/0082322 A1 | 5/2003 | Suzuki et al. | |
| 2004/0176564 A1 | 9/2004 | Yamamoto et al. | |
| 2005/0239997 A1 | 10/2005 | Matsumoto | |
| 2011/0220169 A1* | 9/2011 | Okawara | B32B 27/36 136/244 |
| 2011/0223419 A1 | 9/2011 | Okawara et al. | |
| 2013/0199599 A1 | 8/2013 | Fukuda et al. | |

FOREIGN PATENT DOCUMENTS

| | | | |
|---|---|---|---|
| JP | H08-30119 B2 | 3/1996 | |
| JP | 2543624 B2 | 10/1996 | |
| JP | 2621563 B2 | 6/1997 | |
| JP | 3121876 B2 | 1/2001 | |
| JP | 3136774 B2 | 2/2001 | |
| JP | 3335683 B2 | 10/2002 | |
| JP | 3603585 B2 | 12/2004 | |
| JP | 3616522 B2 | 2/2005 | |
| JP | 3617340 B2 | 2/2005 | |

(Continued)

OTHER PUBLICATIONS

Sikkema, D.J., et al.; Journal of the Royal Netherlands Chemical Society, 1976, p. 154-156.*
H.J. Dillinger et al.; Das Thermodynamisch Kontrollierte Addukt Aus Tert.Butylisonitril Und Acetylendicarbonester; 1974; pp. 2561-2564; vol. 30; Pergamon Press; Great Britain.
Eiichi Sugimoto (editor); Constituent Materials for Sunlight Power Generation System; 2008; Kogyo Chosakai Publishing Co., Ltd.
Official Action Issued by the Japanese Patent Office on Aug. 18, 2015 in connection with JP 2013-228466.

(Continued)

*Primary Examiner* — Robert Jones, Jr.
(74) *Attorney, Agent, or Firm* — Jean C. Edwards, Esq.; Edwards Neils LLC

(57) ABSTRACT

By forming a polyester film from a polyester resin composition including ketene imine compound represented by the following Formula (1) and polyester, the polyester film having excellent hydrolysis resistance in which volatilization of the ketene imine compound or the ketene compound can be suppressed. In Formula (1), $R_1$ and $R_2$ represent an alkyl group, an aryl group, an alkoxy group, an alkoxycarbonyl group, an aminocarbonyl group, an aryloxy group, an acyl group, or an aryloxycarbonyl group, and the $R_1$—C (=C)—$R_2$ substructure has a molecular weight of 320 or greater. $R_3$ represents an alkyl group or an aryl group.

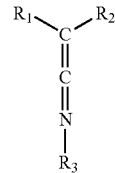

Formula (1)

14 Claims, No Drawings

(56) References Cited

FOREIGN PATENT DOCUMENTS

| | | | |
|---|---|---|---|
| JP | 3680523 | B2 | 8/2005 |
| JP | 3717380 | B2 | 11/2005 |
| JP | 3717392 | B2 | 11/2005 |
| JP | 3897756 | B2 | 3/2007 |
| JP | 2007-210901 | A | 8/2007 |
| JP | 3962226 | B2 | 8/2007 |
| JP | 3979866 | B2 | 9/2007 |
| JP | 3996871 | B2 | 10/2007 |
| JP | 4000867 | B2 | 10/2007 |
| JP | 4053837 | B2 | 2/2008 |
| JP | 4127119 | B2 | 7/2008 |
| JP | 4134710 | B2 | 8/2008 |
| JP | 4159154 | B2 | 10/2008 |
| JP | 4167159 | B2 | 10/2008 |
| JP | 4269704 | B2 | 5/2009 |
| JP | 2009-155479 | A | 7/2009 |
| JP | 2009-158952 | A | 7/2009 |
| JP | 4313538 | B2 | 8/2009 |
| JP | 2010-235824 | A | 10/2010 |
| JP | 2011-256337 | A | 12/2011 |
| JP | 2012-084844 | A | 4/2012 |
| JP | 2014-080561 | A | 5/2014 |
| JP | 2014-129500 | A | 7/2014 |
| KR | 10-1998-0033204 | A | 7/1998 |
| KR | 10-2011-0034665 | A | 4/2011 |

OTHER PUBLICATIONS

Robabeh Baharfar et al.; Three-component reaction of alkyl isocyanides with acetylenic esters and pyridine-2-carboxaldoxime or α-furildioxime: Synthesis and dynamic NMR study of ketenimines and bis(ketenimines); Chinese Chemical Letters; 2011; 22; pp. 943-946; Elsevier.

H.J. Dillinger et al.; Das Kinetisch Kontrollierte Addukt Aus Tert.Butylisonitril Und Acetylendicarbonester; Tetrahedron; 1974; pp. 2553-2559; vol. 30; Pergamon Press; Great Britain.

H.J. Dillinger et al.; Das Thermodynamisch Kontrollierte Addukt Aus Tert.Butylisonitril Und Acetylendicarbonester; Tetrahedron; 1974; pp. 2553-2559; vol. 30; Pergamon Press; Great Britain.

International Preliminary Report on Patentability issued by WIPO on May 12, 2015 in connection with Intl. Patent Application No. PCT/JP2013/079840.

International Search Report issued in PCT/JP2013/079840 on Jan. 28, 2014.

Written Opinion issued in PCT/JP2013/079840 on Jan. 28, 2014.

Calvin L. Stevens and James C. French, Nitrogen Analogs of Ketenes. A New Method of Preparation, J. Am. Chem. Soc., Feb. 5. 1953, pp. 657-660, vol. 75.

Herbert A. Pohl, Determination of Carboxyl End Groups in a Polyester, Polyethylene Terephthalate, Anal. Chem., Oct. 1954, pp. 1614-1616, vol. 26. No. 10, Explosives Department, E.I. du pont de Nemours & Co., Wilmington, Del.

First Office Action issued by the State Intellectual Property Office of People's Republic of China on Nov. 3, 2015, in connection with Chines Patent Application No. 201380056918.1.

Second Office Action issued by the State Intellectual Property Office of People's Republic of China on May 30, 2016, in connection with Chinese Patent Application No. 201380056918.1.

Notice of Grounds for Rejection issued by the Korean Intellectual Property Office on Aug. 12, 2016, in connection with Korean Patent Application No. 2015-7011031.

Decision of Rejection issued by the State Intellectual Property Office of China on Oct. 8, 2016, in connection with Chinese Patent Application No. 201380056918.1.

* cited by examiner

KETENE IMINE COMPOUND, POLYESTER FILM, BACK SHEET FOR SOLAR CELL MODULE AND SOLAR CELL MODULE

CROSS-REFERENCE TO RELATED APPLICATIONS

This application is a Continuation of PCT International Application No. PCT/JP2013/079840, which was published under PCT article 21 (2) in Japanese, filed Nov. 5, 2013, which claims priority under 35 U.S.C. Section 119(a) to Japanese Patent Application No. 2012-244742 filed on Nov. 6, 2012, and Japanese Patent Application No. 2013-228466 filed on Nov. 1, 2013. The above applications are hereby expressly incorporated by reference, in their entirety, into the present application.

TECHNICAL FIELD

The present invention relates to a novel ketene imine compound. The present invention relates to a polyester film containing a novel ketene imine compound, a back sheet for a solar cell module having the polyester film, and a solar cell module obtained by laminating the back sheet for a solar cell module.

BACKGROUND ART

A solar cell module generally has a structure in which from the light-receiving surface side to which sunlight is incident, a glass or front sheet/a transparent filling material (sealing material)/a solar cell element/a sealing material/a back sheet are laminated in this order. Specifically, the solar cell element is generally embedded with a resin (sealing material) such as EVA (an ethylene-vinyl acetate copolymer) and the like, and a protective sheet for a solar cell is adhered thereto. The protective sheet for a solar cell, above all, a back sheet for a solar cell module, which becomes in particular an outermost layer, is considered to be under an environment exposed to weather outdoor or direct sunlight for a long period of time, and therefore, excellent weather resistance (wet heat resistance, heat resistance) is required.

As the back sheet for a solar cell module, in the related art, a polyester film, in particular, a polyethylene terephthalate (hereinafter, referred to as PET) film has been used. The polyester film has excellent heat resistance, mechanical characteristics, chemical resistance, and the like, and therefore, the polyester film is widely used industrially. However, since the film has poor hydrolysis resistance, the molecular weight is reduced by hydrolysis, and mechanical characteristics are reduced by progressively stiffening. Therefore, it was not possible to maintain a practical strength for a long period of time as a back sheet for a solar cell.

In order to solve the above problems, for example, Patent Document 1 discloses the use of a ketene imine compound as a terminal blocking agent of the polyester in order to suppress hydrolysis of polyester. Here, it is proposed that hydrolysis of polyester is suppressed by reacting the ketene imine compound with the terminal carboxyl group of polyester.

RELATED ART DOCUMENT

Patent Document

[Patent Document 1] U.S. Pat. No. 3,692,745

SUMMARY OF INVENTION

Technical Problem

However, from the study of the inventors of the present invention, it was found that when the ketene imine compound disclosed in Patent Document 1 and the terminal carboxyl group of polyester were allowed to react, a part of the added ketene imine compound volatilized. If a part of the ketene imine compound volatilizes, the reaction with the terminal carboxyl group does not sufficiently proceed, and the ketene imine compound does not sufficiently function as a terminal blocking agent, and therefore, this becomes a problem.

On the other hand, by the reaction of the ketene imine compound remaining without being volatilized with the terminal carboxyl group of polyester, a ketene compound is produced as a byproduct. From the study of the inventors, it was found that, in the production step of a polyester film, the ketene compound produced in such a manner as a byproduct is also volatilized. That is, in the production step of a polyester film including a ketene imine compound in the related art as a terminal blocking agent, the ketene imine compound or the ketene compound volatilizes as a gas in the production step, and therefore, this becomes a problem.

Therefore, in order to solve the problems in the related art, the inventors have conducted studies for the purpose of providing a polyester film having excellent hydrolysis resistance in which volatilization of the ketene imine compound or the ketene compound can be suppressed.

Solution to Problem

The inventors have made earnest investigations for solving the problems. As a result, the inventors have found that a polyester film having excellent hydrolysis resistance in which volatilization of the ketene imine compound or the ketene compound can be suppressed may be produced by using a polyester resin composition including ketene imine compound that has a certain level or higher of molecular weight.

Specifically, the invention includes the following aspects.
[1] A polyester resin composition including a ketene imine compound represented by the following Formula (1) and polyester;

Formula (1)

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 320 or greater; and $R_3$ represents an alkyl group which may have a substituent or an aryl group which may have a substituent.

[2] The polyester resin composition according to [1], wherein the ketene imine compound is represented by the following Formula (2);

Formula (2)

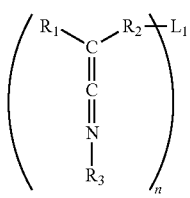

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent; $R_3$ represents an alkyl group which may have a substituent or an aryl group which may have a substituent; n represents an integer of 1 to 4, and $L_1$ represents an n valent group; and the $(R_1-C(=C)-R_2-)_n-L_1$ substructure has a molecular weight of 320 or greater.

[3] The polyester resin composition according to [2], wherein n in the formula (2) represents an integer of 3 or 4.

[4] The polyester resin composition according to [1], wherein the ketene imine compound is represented by the following Formula (3);

Formula (3)

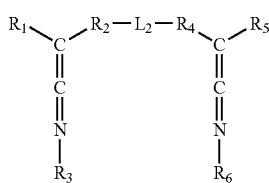

wherein $R_1$ and $R_5$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ and $R_4$ each independently represents an alkyl group which has $L_2$ as a substituent, an aryl group which has $L_2$ as a substituent, an alkoxy group which has $L_2$ as a substituent, an alkoxycarbonyl group which has $L_2$ as a substituent, an aminocarbonyl group which has $L_2$ as a substituent, an aryloxy group which has $L_2$ as a substituent, an acyl group which has $L_2$ as a substituent, or an aryloxycarbonyl group which has $L_2$ as a substituent; $R_3$ and $R_6$ each independently represents an alkyl group which may have a substituent or an aryl group which may have a substituent; $L_2$ represents a single bond or a divalent linking group; and the $R_1-C(=C)-R_2-L_2-R_4-C(=C)-R_5$ substructure has a molecular weight of 320 or greater.

[5] A ketene imine compound represented by the following Formula (4);

Formula (4)

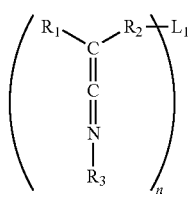

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent; $R_3$ represents an alkyl group which may have a substituent or an aryl group which may have a substituent; n represents an integer of 2 to 4, and $L_1$ represents an n valent linking group.

[6] The ketene imine compound according to [5], wherein the ketene imine compound is represented by the following Formula (5);

Formula (5)

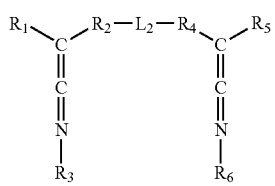

wherein $R_1$ and $R_5$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ and $R_4$ each independently represents an alkyl group which has $L_2$ as a substituent, an aryl group which has $L_2$ as a substituent, an alkoxy group which has $L_2$ as a substituent, an alkoxycarbonyl group which has $L_2$ as a substituent, an aminocarbonyl group which has $L_2$ as a substituent, an aryloxy group which has $L_2$ as a substituent, an acyl group which has $L_2$ as a substituent, or an aryloxycarbonyl group which has $L_2$ as a substituent; $R_3$ and $R_6$ each independently represents an alkyl group which may have a substituent or an aryl group which may have a substituent; and $L_2$ represents a single bond or a divalent linking group.

[7] A polyester film formed of a polyester resin composition including a ketene imine compound represented by the following Formula (1) and polyester;

Formula (1)

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 320 or greater; and $R_3$ represents an alkyl group which may have a substituent or an aryl group which may have a substituent.

[8] A back sheet for a solar cell module having a polyester film formed of a polyester resin composition including a ketene imine compound represented by the following general Formula (1) and polyester;

Formula (1)

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 320 or greater; and $R_3$ represents an alkyl group which may have a substituent or an aryl group which may have a substituent.

[9] A solar cell module having a back sheet having a polyester film formed of a polyester resin composition including a ketene imine compound represented by the following general Formula (1) and polyester;

Formula (1)

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 320 or greater; and $R_3$ represents an alkyl group which may have a substituent or an aryl group which may have a substituent.

Advantageous Effects of Invention

According to the invention, by forming a polyester film from a polyester resin composition including ketene imine compound that has a specific structure, generation of gas derived from the ketene imine compound can be suppressed. By this, the reaction of the ketene imine compound with the terminal carboxyl group of polyester is promoted, and thereby hydrolysis resistance of a polyester film is enhanced. Generation of gas derived from ketene imine compound can be suppressed, and thereby operational safety in production can be improved

DESCRIPTION OF EMBODIMENTS

The invention will be described in detail below. The descriptions for the constitutional elements shown below may be based on representative embodiments and specific examples, but the invention is not limited to the embodiments. The numerical range herein expressed with numerical values includes the numerical values as the lower limit and the upper limit.

(Ketene Imine Compound)

The ketene imine compound of the present invention is represented by the following Formula (1).

Formula (1)

Here, in Formula (1), $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 320 or greater. $R_3$ represents an alkyl group which may have a substituent or an aryl group which may have a substituent.

The alkyl group which is represented by $R_1$ or $R_2$ is preferably an alkyl group having 1 to 20 carbon atoms, and more preferably an alkyl group having 1 to 12 carbon atoms. Moreover, the number of carbon atoms of the alkyl group which is represented by $R_1$ or $R_2$ represents the number of carbon atoms in which the number of carbon atoms of the substituent is not included. The alkyl group which is represented by $R_1$ or $R_2$ may be a linear alkyl group, a branched alkyl group, or a cyclic alkyl group. Examples of the alkyl group which is represented by $R_1$ or $R_2$ can include a methyl group, an ethyl group, an n-propyl group, an iso-propyl group, an n-butyl group, a tert-butyl group, a sec-butyl group, an iso-butyl group, an n-pentyl group, a sec-pentyl group, an iso-pentyl group, an n-hexyl group, a sec-hexyl group, an iso-hexyl group, and a cyclohexyl group. Among these, a methyl group, an ethyl group, an n-propyl group, an iso-propyl group, an iso-butyl group, and a cyclohexyl group are more preferable.

The aryl group which is represented by $R_1$ or $R_2$ is preferably an aryl group having 6 to 20 carbon atoms, and more preferably an aryl group having 6 to 12 carbon atoms. Moreover, the number of carbon atoms of the aryl group which is represented by $R_1$ or $R_2$ represents the number of carbon atoms in which the number of carbon atoms of the substituent is not included. Examples of the aryl group which is represented by $R_1$ or $R_2$ can include a phenyl group and a naphthyl group, and among these, a phenyl group is particularly preferable.

The alkoxy group which is represented by $R_1$ or $R_2$ is preferably an alkoxy group having 1 to 20 carbon atoms, more preferably an alkoxy group having 1 to 12 carbon atoms, and particularly preferably an alkoxy group having 2 to 6 carbon atoms. Moreover, the number of carbon atoms of the alkoxy group which is represented by $R_1$ or $R_2$ represents the number of carbon atoms in which the number of carbon atoms of substituent is not included. The alkoxy group which is represented by $R_1$ or $R_2$ may be a linear alkoxy group, a branched alkoxy group, or a cyclic alkoxy group. Preferable examples of the alkoxy group which is represented by $R_1$ or $R_2$ can include a group in which —O— is linked to the terminal of an alkyl group which is represented by $R_1$ or $R_2$.

The alkoxycarbonyl group which is represented by $R_1$ or $R_2$ is preferably an alkoxycarbonyl group having 2 to 20 carbon atoms, more preferably an alkoxycarbonyl group having 2 to 12 carbon atoms, and particularly preferably an alkoxycarbonyl group having 2 to 6 carbon atoms. Moreover, the number of carbon atoms of the alkoxycarbonyl group which is represented by $R_1$ or $R_2$ represents the number of carbon atoms in which the number of carbon atoms of substituent is not included. As the alkoxy moiety of the alkoxycarbonyl group which is represented by $R_1$ or $R_2$, the examples of the alkoxy group described above can be exemplified.

The aminocarbonyl group which is represented by $R_1$ or $R_2$ is preferably an alkyl aminocarbonyl group having 1 to 20 carbon atoms, and more preferably an aryl aminocarbonyl group having 6 to 20 carbon atoms. Moreover, the number of carbon atoms of the alkyl aminocarbonyl group which is represented by $R_1$ or $R_2$ represents the number of carbon atoms in which the number of carbon atoms of substituent is not included. Preferable examples of the alkyl amino moiety of the alkyl aminocarbonyl group can include a group in which —NH— is linked to the terminal of an alkyl group which is represented by $R_1$ or $R_2$.

Preferable examples of the aryl amino moiety of the aryl aminocarbonyl group having 6 to 20 carbon atoms can include a group in which —NH— is linked to the terminal of an aryl group which is represented by $R_1$ or $R_2$.

The aryloxy group which is represented by $R_1$ or $R_2$ is preferably an aryloxy group having 6 to 20 carbon atoms, and more preferably an aryloxy group having 6 to 12 carbon atoms. Moreover, the number of carbon atoms of the aryloxy group which is represented by $R_1$ or $R_2$ represents the number of carbon atoms in which the number of carbon atoms of substituent is not included. As the aryl moiety of the arylxoy group which is represented by $R_1$ or $R_2$, the examples of the aryl group described above can be exemplified.

The acyl group which is represented by $R_1$ or $R_2$ is preferably an acyl group having 2 to 20 carbon atoms, more preferably an acyl group having 2 to 12 carbon atoms, and particularly preferably an acyl group having 2 to 6 carbon atoms. Moreover, the number of carbon atoms of the acyl group which is represented by $R_1$ or $R_2$ represents the number of carbon atoms in which the number of carbon atoms of substituent is not included.

The aryloxycarbonyl group which is represented by $R_1$ or $R_2$ is preferably an aryloxycarbonyl group having 7 to 20 carbon atoms, and more preferably an aryloxycarbonyl group having 7 to 12 carbon atoms. Moreover, the number of carbon atoms of the aryoxycarbonyl group which is represented by $R_1$ or $R_2$ represents the number of carbon atoms in which the number of carbon atoms of substituent is not included. As the aryl moiety of the aryloxycarbonyl group which is represented by $R_1$ or $R_2$, the examples of the aryl group described above can be exemplified.

Each group which is represented by $R_1$ or $R_2$ may have a substituent. The substituent is not particularly limited as long as a reaction between a ketene imine group and a carboxyl group can proceed. In addition, the substituent may include a ketene imine moiety, or may include a plurality of ketene imine moieties.

Furthermore, the ketene imine structure which is represented by the following Formula (1) may be included in each group which is represented by $R_1$ or $R_2$ as a repeating unit. For example, the ketene imine compound used in the present invention may be a compound in which repeating units in which each of $R_1$ and $R_2$ in Formula (1) is formed of a divalent linking group are linked in a chain form or in a cyclic form or may be a compound in which repeating units in which each of $R_2$ and $R_3$ in Formula (1) is formed of a divalent linking group are linked in a chain form or in a cyclic form.

$R_3$ represents an alkyl group which may have a substituent or an aryl group which may have a substituent. The alkyl group is preferably an alkyl group having 1 to 20 carbon atoms, and more preferably an alkyl group having 1 to 12 carbon atoms. Moreover, the number of carbon atoms of the alkyl group which is represented by $R_3$ represents the number of carbon atoms in which the number of carbon atoms of substituent is not included. The alkyl group which is represented by $R_3$ may be a linear alkyl group, a branched alkyl group, or a cyclic alkyl group. Examples of the alkyl group which is represented by $R_3$ can include a methyl group, an ethyl group, an n-propyl group, an iso-propyl group, an n-butyl group, a tert-butyl group, a sec-butyl group, an iso-butyl group, an n-pentyl group, a sec-pentyl group, an iso-pentyl group, an n-hexyl group, a sec-hexyl group, an iso-hexyl group, and a cyclohexyl group. Among these, a methyl group, an ethyl group, an n-propyl group, an iso-propyl group, an n-butyl group, an iso-butyl group, and a cyclohexyl group are more preferable.

The aryl group is preferably an aryl group having 6 to 20 carbon atoms, and more preferably an aryl group having 6 to 12 carbon atoms. Examples of the aryl group which is represented by $R_3$ can include a phenyl group and a naphthyl group, and among these, a phenyl group is particularly preferable.

Each group which is represented by $R_3$ may have a substituent. The substituent is not particularly limited as long as a reaction between a ketene imine group and a carboxyl group can proceed.

Moreover, $R_1$ or $R_2$, and $R_3$ in Formula (1) may form a cyclic structure by being linked to each other. In this case, the cyclic structure may include a ketene imine moiety, or a repeating unit having the structure which is represented by Formula (1).

The $R_1$—C(=C)—$R_2$ substructure in the ketene imine compound which is represented by Formula (1) has a molecular weight of 320 or greater. Moreover, in a case where the ketene imine structure is included in $R_1$ or $R_2$, the ketene imine structure is converted to the corresponding ketene structure, and the molecular weight of the structure excluding the oxygen atom constituting the ketene structure is taken as the molecular weight of the $R_1$—C(=C)—$R_2$ substructure.

In addition, the ketene imine compound used in the present invention is preferably the compound which is represented by the following Formula (2).

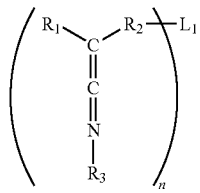

Formula (2)

Here, in Formula (2), $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent. $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent. $R_3$ represents an alkyl group which may have a substituent or an aryl group which may have a substituent. n represents an integer of 1 to 4, and $L_1$ represents an n valent group. The $(R_1$—C(=C)—$R_2$—$)_n$-$L_1$ substructure has a molecular weight of 320 or greater.

$R_1$ in Formula (2) has the same meaning as that in Formula (1), and the preferable range thereof is also the same.

In Formula (2), $R_2$ represents an alkyl group, an aryl group, an alkoxy group, an alkoxycarbonyl group, an aminocarbonyl group, an aryloxy group, an acyl group, or an aryloxycarbonyl group having $L_1$ which is an n valent group. The alkyl group, the aryl group, the alkoxy group, the alkoxycarbonyl group, the aminocarbonyl group, the aryloxy group, the acyl group, or the aryloxycarbonyl group has the same meaning as that in Formula (1), and the preferable range thereof is also the same.

In addition, $R_2$ may further have a substituent in addition to $L_1$, and the substituent is not particularly limited as long as a reaction between a ketene imine group and a carboxyl group can proceed. In addition, the substituent of $R_1$ or $R_2$ may be a substituent in which $R_1$ and $R_2$ are linked to each other.

$R_3$ in Formula (2) has the same meaning as that in Formula (1), and the preferable range thereof is also the same.

$L_1$ represents an n valent group, and n represents an integer of 1 to 4. Among these, n is preferably 2 to 4. Moreover, in a case where n is 1, $L_1$ represents a monovalent group, and in a case where n is 2 to 4, $L_1$ represents a di- to tetravalent linking group.

Specific examples of the divalent linking group include a group which is represented by —$NR_8$— ($R_8$ represents a hydrogen atom, an alkyl group which may have a substituent, or an aryl group which may have a substituent, and a hydrogen atom is preferable), —$SO_2$—, —CO—, a substituted or unsubstituted alkylene group, a substituted or unsubstituted alkenylene group, an alkynylene group, a substituted or unsubstituted phenylene group, a substituted or unsubstituted biphenylene group, a substituted or unsubstituted naphthylene group, —O—, —S—, —SO—, and a group obtained by combining two or more of these.

Specific examples of the trivalent linking group include a group obtained by removing one hydrogen atom from a group having a substituent among the linking groups exemplified as the divalent linking group.

Specific examples of the tetravalent linking group include a group obtained by removing two hydrogen atoms from a group having a substituent among the linking groups exemplified as the divalent linking group.

In the present invention, when n is 2 to 4, a compound having two or more ketene imine moieties in one molecule can be obtained, and a further improved terminal blocking effect can be exhibited. In addition, when a compound has two or more ketene imine moieties in one molecule, the molecular weight per ketene imine group can be reduced, and the ketene imine compound and a terminal carboxyl group of polyester can be efficiently reacted. Furthermore, when a compound has two or more ketene imine moieties in one molecule, volatilization of the ketene imine compound or the ketene compound can be suppressed.

In Formula (2), n is more preferably 3 or 4. When n is 3 or 4, three or four ketene imine moieties are included in one molecule, and the ketene imine compound can exhibit a further improved terminal blocking effect. In addition, when n is 3 or 4, volatilization of the ketene imine compound can be suppressed even in a case where the molar molecular weight of the substituent of $R_1$ or $R_2$ in Formula (2) is reduced.

In addition, in Formula (2), n is particularly preferably 4. Four ketene imine moieties are included in one molecule, and the ketene imine compound can exhibit a further improved terminal blocking effect. In addition, volatilization of the ketene imine compound can be more effectively suppressed.

The ketene imine compound used in the present invention is preferably a compound represented by the following Formula (3).

Formula (3)

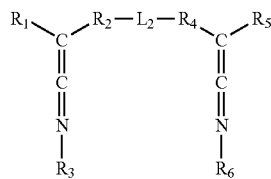

In Formula (3), $R_1$ and $R_5$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent. $R_2$ and $R_4$ each independently represents an alkyl group which has $L_2$ as a substituent, an aryl group which has $L_2$ as a substituent, an alkoxy group which has $L_2$ as a substituent, an alkoxycarbonyl group which has $L_2$ as a substituent, an aminocarbonyl group which has $L_2$ as a substituent, an aryloxy group which has $L_2$ as a substituent, an acyl group which has $L_2$ as a substituent, or an aryloxycarbonyl group which has $L_2$ as a substituent. $R_3$ and $R_6$ each independently represents an alkyl group which may have a substituent or an aryl group which may have a substituent. $L_2$ represents a single bond or a divalent linking group. The $R_1$—C(=C)—$R_2$-$L_2$-$R_4$—C(=C)—$R_5$ substructure has a molecular weight of 320 or greater.

$R_1$ in Formula (3) has the same meaning as that in Formula (1), and the preferable range thereof is also the same. In addition, $R_5$ has the same meaning as $R_1$ in Formula (1), and the preferable range thereof is also the same.

$R_2$ in Formula (3) has the same meaning as that in Formula (2), and the preferable range thereof is also the same. In addition, $R_4$ has the same meaning as $R_2$ in Formula (2), and the preferable range thereof is also the same.

$R_3$ in Formula (3) has the same meaning as that in Formula (1), and the preferable range thereof is also the same. In addition, $R_6$ has the same meaning as $R_3$ in Formula (1), and the preferable range thereof is also the same.

$L_2$ in Formula (3) represents a single bond or a divalent linking group. Specific examples of the divalent linking group can include linking groups exemplified as $L_1$ in Formula (2).

The present invention relates to the ketene imine compound which is represented by the following Formula (4).

Formula (4)

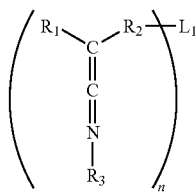

In Formula (4), $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent. $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent. $R_3$ represents an alkyl group which may have a substituent or an aryl group which may have a substituent. n represents an integer of 2 to 4, and $L_1$ represents an n valent linking group.

$R_1$ in Formula (4) has the same meaning as that in Formula (1), and the preferable range thereof is also the same.

$R_2$ in Formula (4) has the same meaning as that in Formula (2), and the preferable range thereof is also the same.

$R_3$ in Formula (4) has the same meaning as that in Formula (1), and the preferable range thereof is also the same.

$L_1$ represents an n valent linking group, and n represents an integer of 2 to 4. Among these, n is preferably 3 or 4, and more preferably 4.

In addition, the present invention relates to the ketene imine compound which is represented by the following Formula (5).

Formula (5)

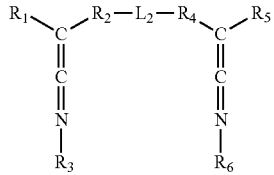

In Formula (5), $R_1$ and $R_5$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent. $R_2$ and $R_4$ each independently represents an alkyl group which has $L_2$ as a substituent, an aryl group which has $L_2$ as a substituent, an alkoxy group which has $L_2$ as a substituent, an alkoxycarbonyl group which has $L_2$ as a substituent, an aminocarbonyl group which has $L_2$ as a substituent, an aryloxy group which has $L_2$ as a substituent, an acyl group which has $L_2$ as a substituent, or an aryloxycarbonyl group which has $L_2$ as a substituent. $R_3$ and $R_6$ each independently represents an alkyl group which may have a substituent or an aryl group which may have a substituent. $L_2$ represents a single bond or a divalent linking group.

$R_1$ in Formula (5) has the same meaning as that in Formula (1), and the preferable range thereof is also the same. In addition, $R_5$ has the same meaning as $R_1$ in Formula (1), and the preferable range thereof is also the same.

$R_2$ in Formula (5) has the same meaning as that in Formula (2), and the preferable range thereof is also the same. In addition, $R_4$ has the same meaning as $R_2$ in Formula (2), and the preferable range thereof is also the same.

$R_3$ in Formula (5) has the same meaning as that in Formula (1), and the preferable range thereof is also the same. In addition, $R_6$ has the same meaning as $R_3$ in Formula (1), and the preferable range thereof is also the same.

$L_2$ in Formula (5) represents a single bond or a divalent linking group. Specific examples of the divalent linking group can include linking groups exemplified as $L_1$ in Formula (2).

In the present invention, the molecular weight of the substituent on the ketene imine moiety carbon in a ketene imine compound is preferably 320 or greater. The molecular weight of the substituent on the ketene imine moiety carbon in a ketene imine compound may be 320 or greater, is preferably 400 or greater, and more preferably 500 or greater. In addition, the molar molecular weight (molar molecular weight/number of ketene imine moiety) of the ketene imine compound to the number of the ketene imine moiety in one molecule is preferably 1000 or less, more preferably 500 or less, and still more preferably 400 or less. In the present invention, when the molecular weight of the substituent on the ketene imine moiety carbon in a ketene imine compound and the molar molecular weight of the ketene imine compound to the number of the ketene imine moiety are within the above-described ranges, volatilization of the ketene imine compound itself can be suppressed, volatilization of the ketene compound produced when blocking the terminal carboxyl group of polyester can be suppressed, and blocking of the terminal carboxyl group of polyester can be performed at a low addition amount of ketene imine compound.

The ketene imine compound of the present invention is a compound having at least one ketene imine group, and for example, the ketene imine compound can be synthesized by referencing a method described in J. Am. Chem. Soc., 1953, 75 (3), pp. 657-660.

Preferable specific examples of the Formula (1) are shown below, but the present invention is not limited thereto.

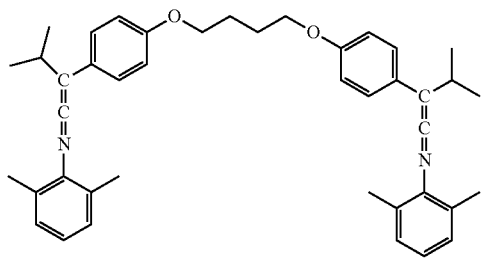

Exemplary Compound (1)

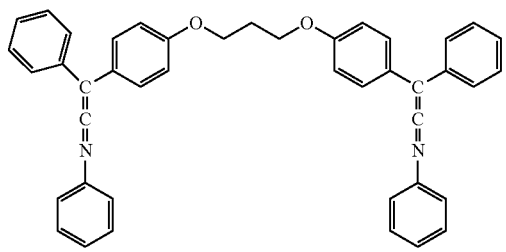

Exemplary Compound (2)

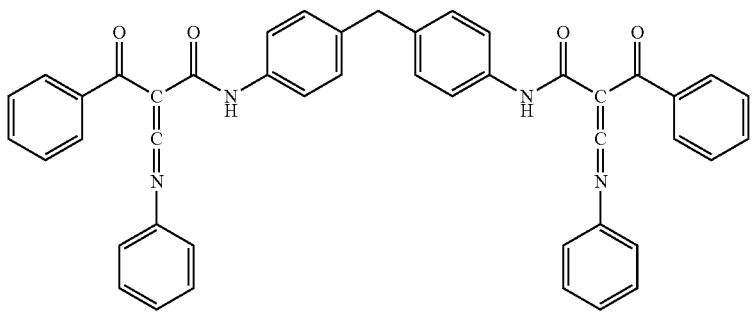

Exemplary Compound (3)

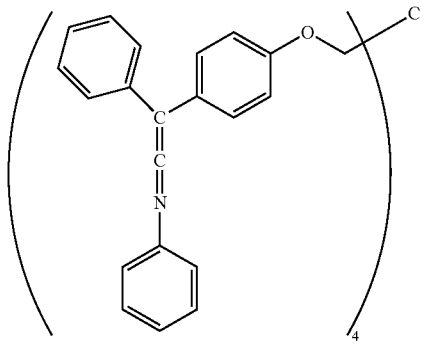

Exemplary Compound (4)

-continued
Exemplary Compound (5)
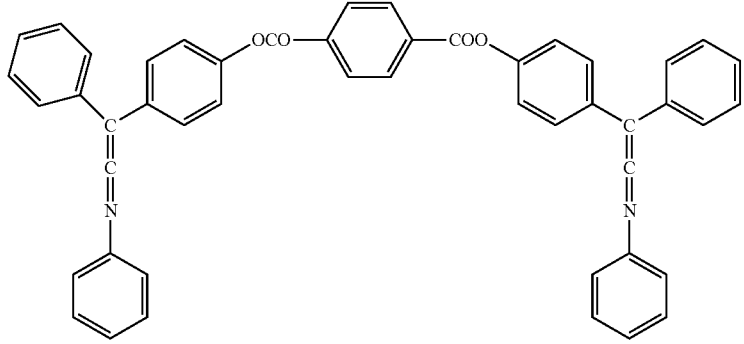
Exemplary Compound (6)
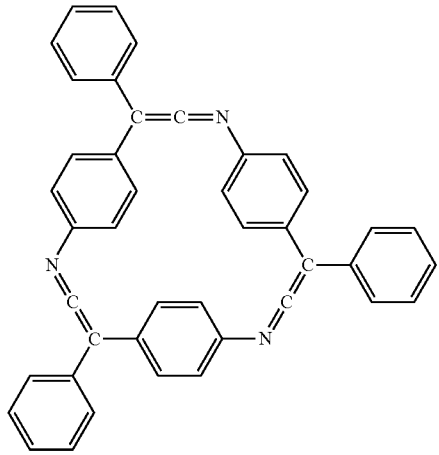
Exemplary Compound (7)
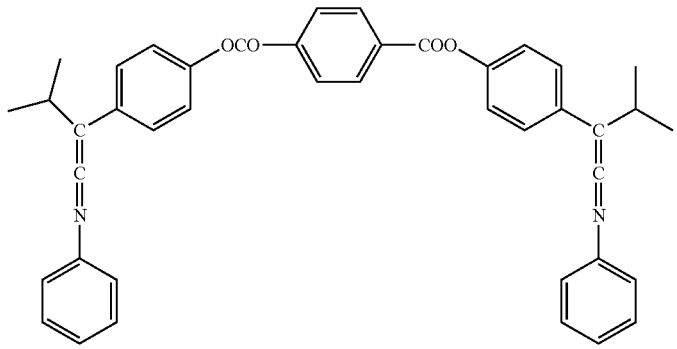
Exemplary Compound (8)
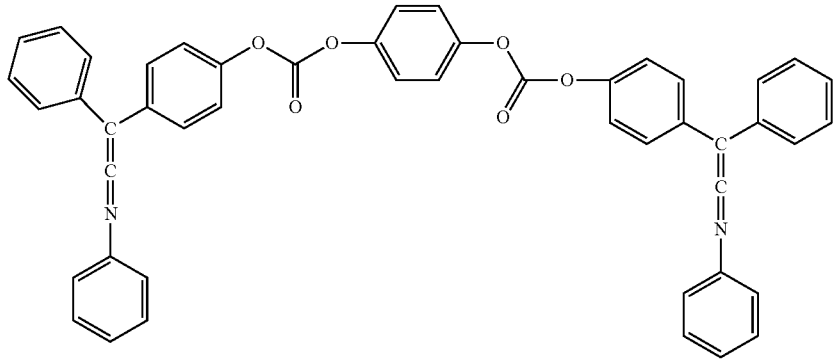

-continued
Exemplary Compound (9)
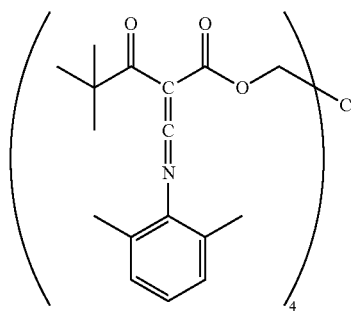
Exemplary Compound (10)
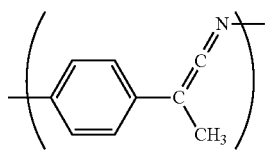
Exemplary Compound (11)
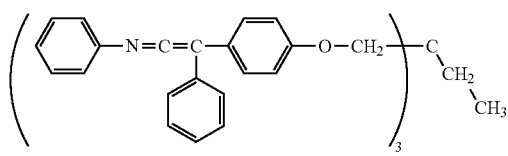
Exemplary Compound (12)
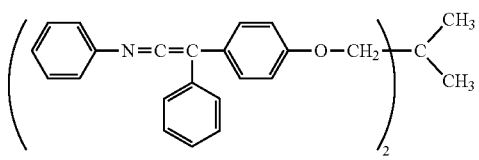
Exemplary Compound (13)
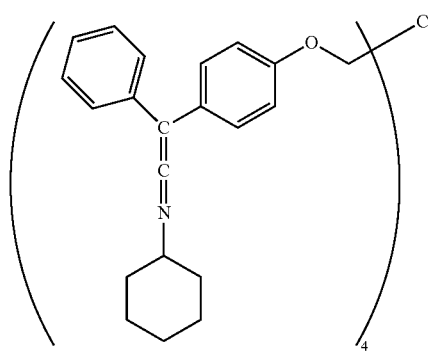
Exemplary Compound (14)
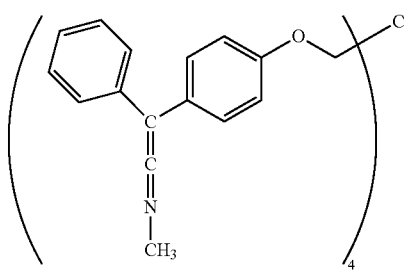
Exemplary Compound (15)
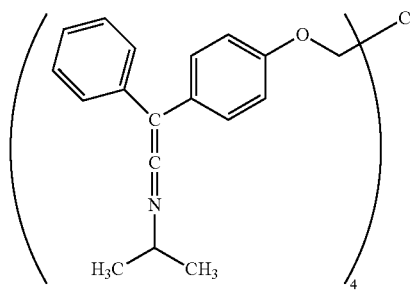
Exemplary Compound (16)
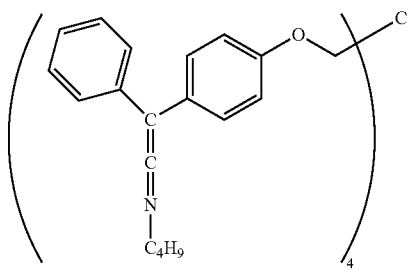
Exemplary Compound (17)
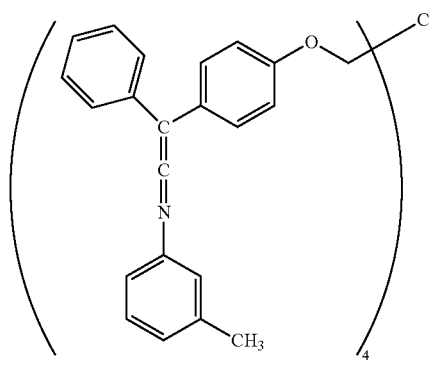
Exemplary Compound (18)
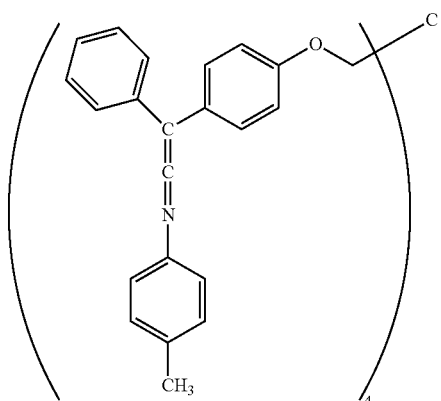

-continued
Exemplary Compound (19)
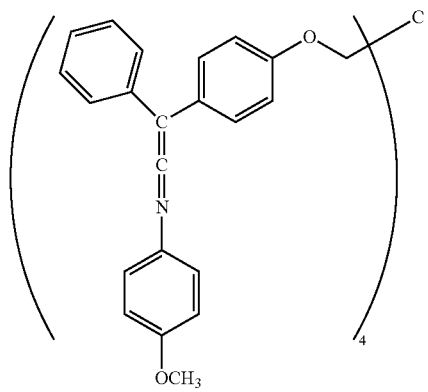
Exemplary Compound (20)
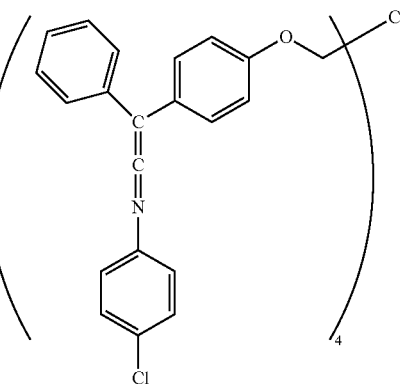
Exemplary Compound (21)
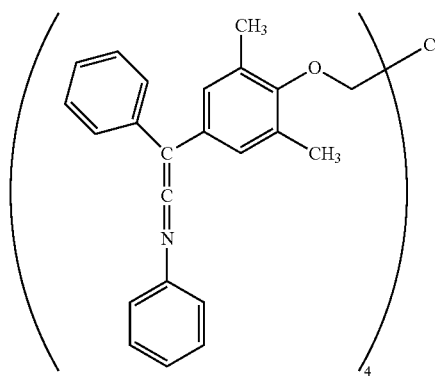
Exemplary Compound (22)
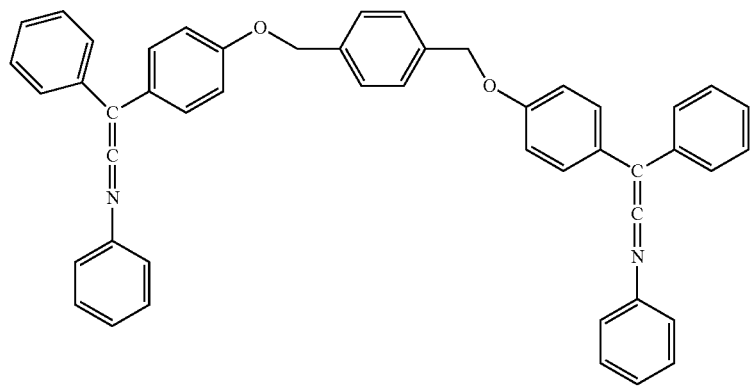
Exemplary Compound (23)
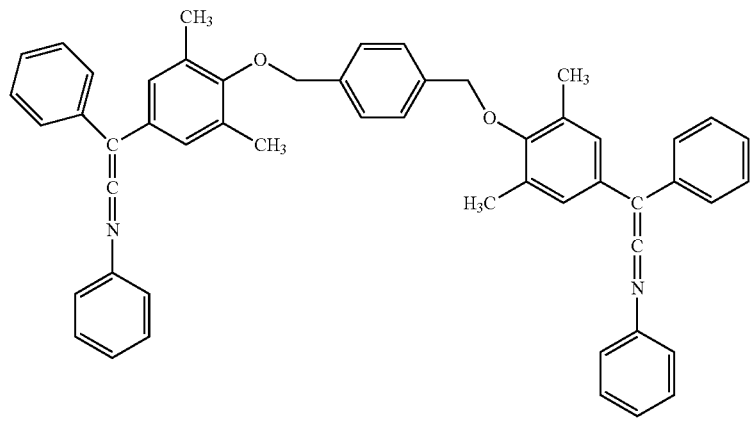

-continued
Exemplary Compound (24)
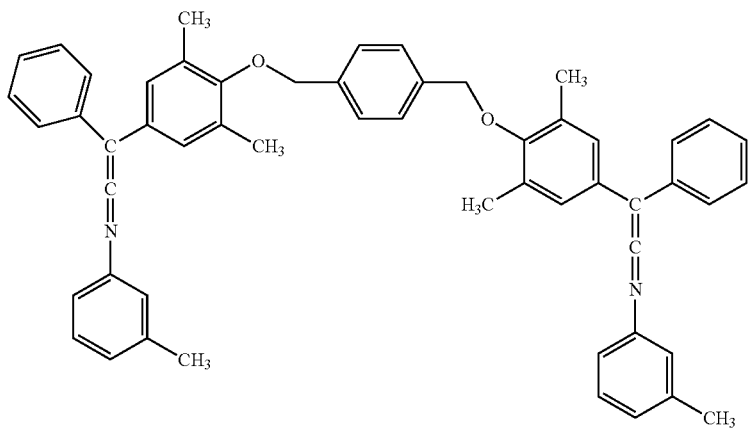
Exemplary Compound (25)
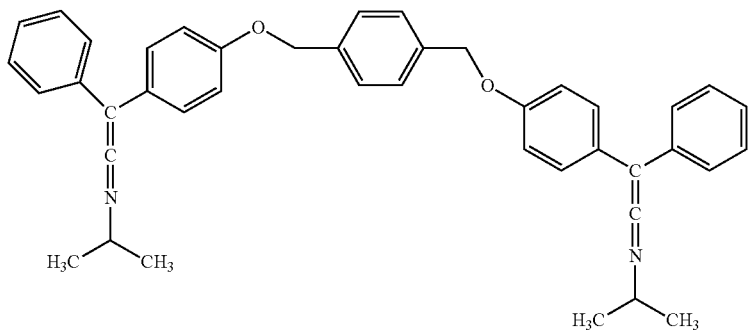
Exemplary Compound (26)
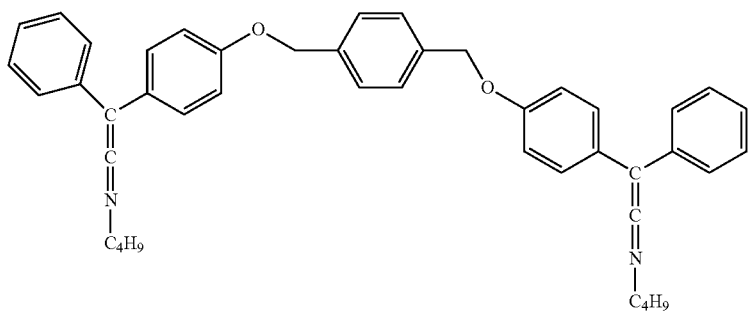
Exemplary Compound (27)
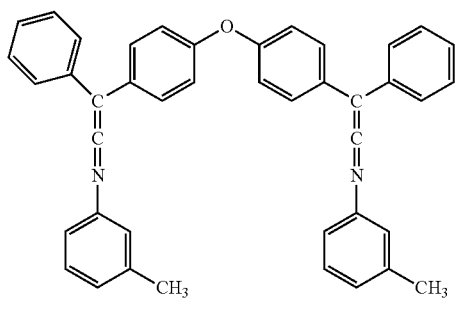
Exemplary Compound (28)
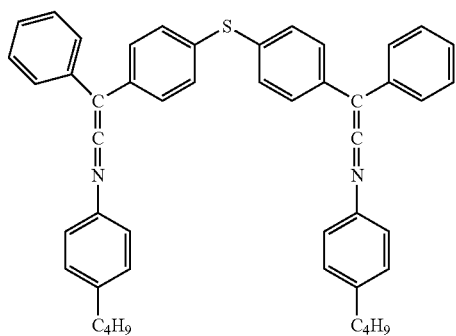

-continued
Exemplary Compound (29)
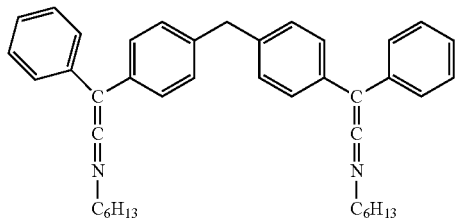
Exemplary Compound (30)
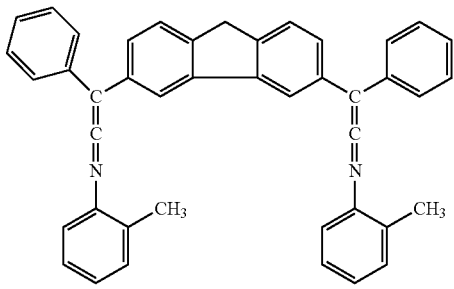
Exemplary Compound (31)
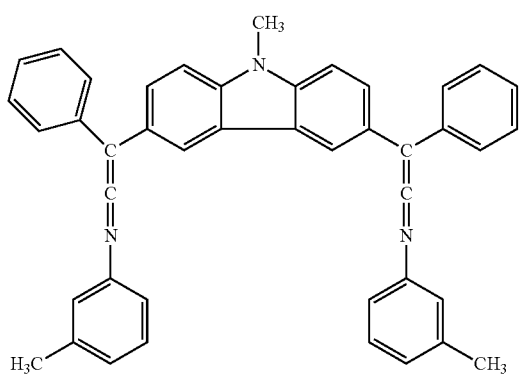
Exemplary Compound (32)
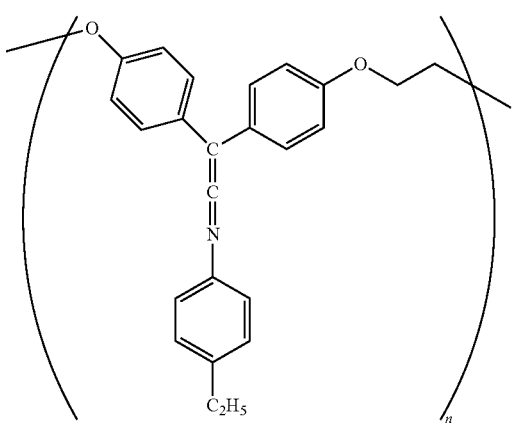
Exemplary Compound (33)
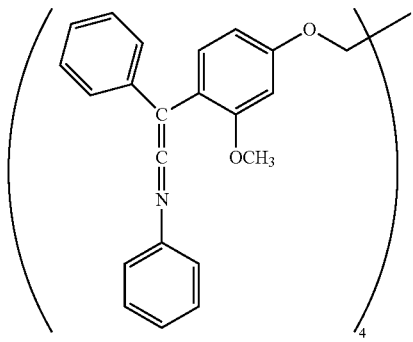
Exemplary Compound (34)
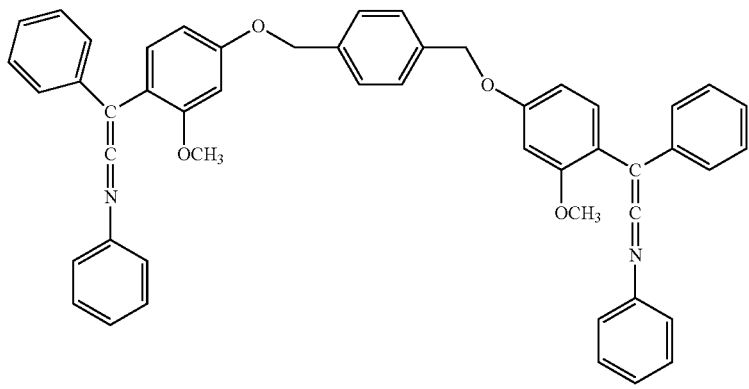

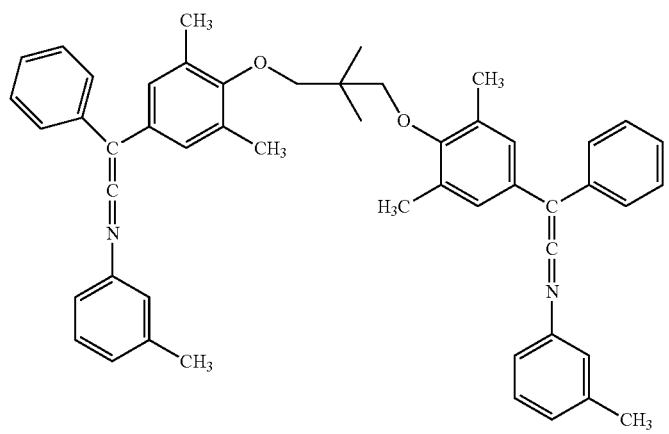
Exemplary Compound (35)
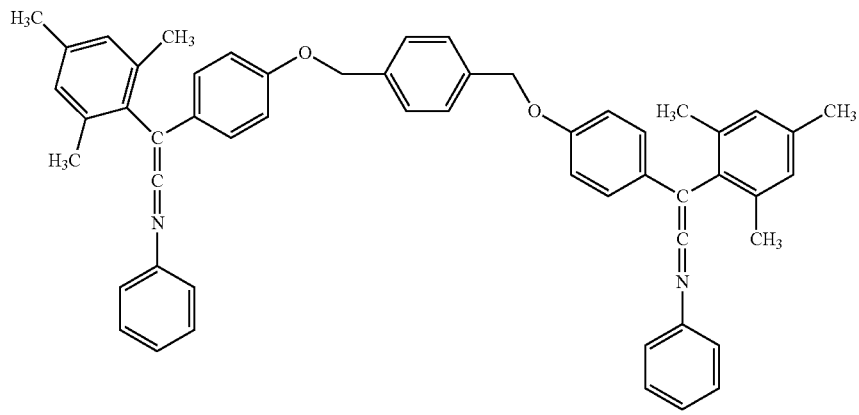
Exemplary Compound (36)
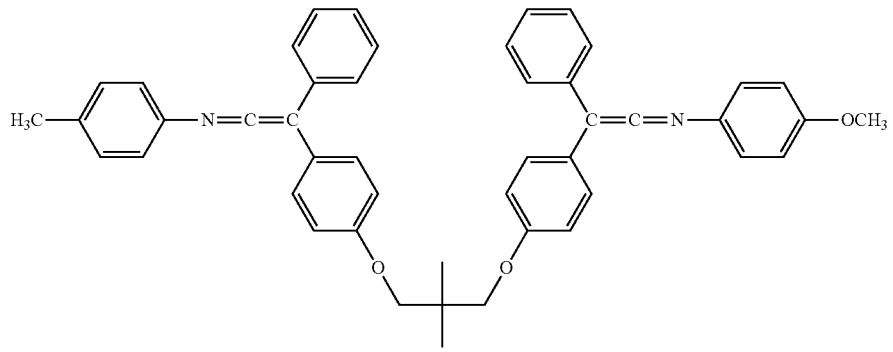
Exemplary Compound (37)
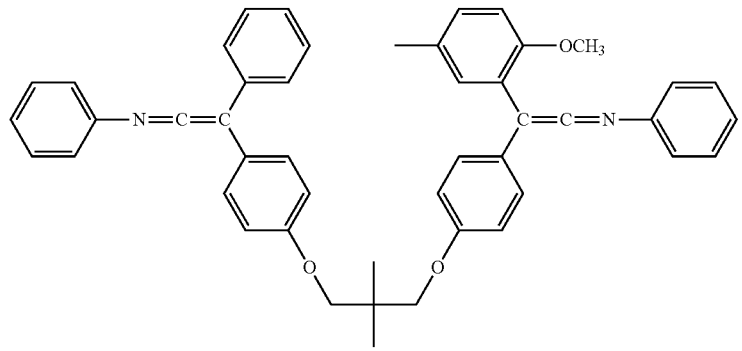
Exemplary Compound (38)

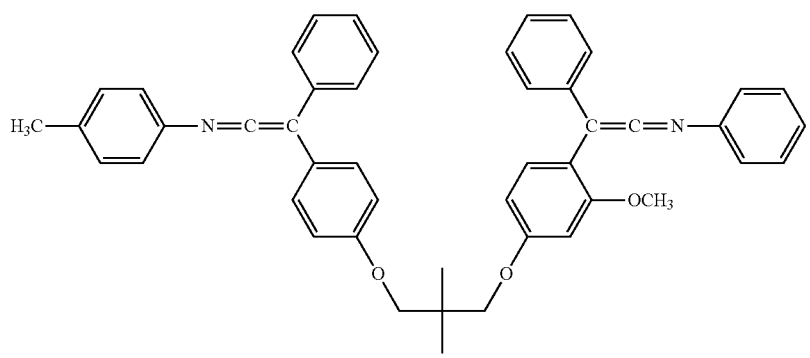

Exemplary Compound (39)

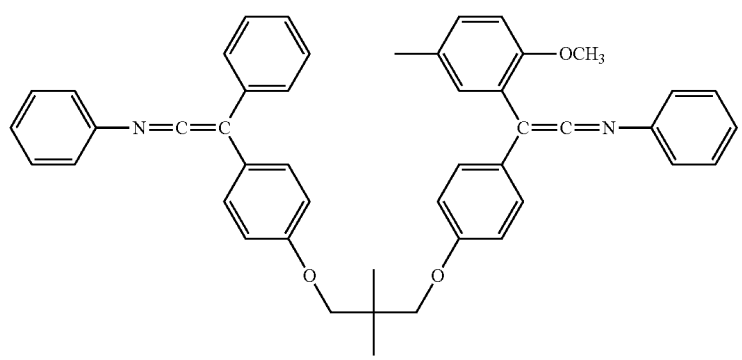

Exemplary Compound (40)

In the present invention, the ketene imine compound is more preferably tri- or tetrafunctional, and still more preferably tetrafunctional. As a result, the terminal blocking effect can be further enhanced, and volatilization of the ketene imine compound or the ketene compound can be more effectively suppressed. Here, the functional group number represents the number of the ketene imine moieties included in a compound, and a trifunctional ketene imine compound means a compound including three ketene imine moieties.

$R_1$ or $R_2$, and $R_3$ in Formula (1) may form a cyclic structure by being linked to each other. For example, in the case of having a cyclic structure which has a ketene imine moiety as a ring skeleton as Exemplary Compound (6), $R_1$ or $R_2$, and $R_3$ form a cyclic structure by being linked to each other, and $R_3$ consists of an alkylene group or an arylene group having a ring skeleton. In this case, $R_1$ or $R_2$ has a linking group including a ketene imine moiety.

In addition, the ketene imine compound may be a polymer. For example, Exemplary Compound (10) or Exemplary Compound (32) shows a repeating unit having the repetition number of n, and n represents an integer of 3 or greater. Moreover, the left terminal in Exemplary Compound (10) is a hydrogen atom, and the right terminal is a phenyl group.

(Chemical Modification Method of Polyester Terminal Carboxyl Group)

Chemical modification of a polyester terminal carboxyl group of the present invention can be performed by mixing the ketene imine compound which is represented by Formula (1) and polyester in a melt state.

It is described in U.S. Pat. No. 3,692,745 that the ketene imine compound and polyester are mixed in a melt state, and it is a known method. According to U.S. Pat. No. 3,692,745, in the case of mixing the ketene imine compound and polyester in a melt state, as the following reaction scheme, an imide compound (1) is produced by the reaction of the ketene imine group with polyester-COOH. By the mechanism, the polyester terminal carboxyl group is blocked.

However, as a result of thorough examination, the present inventors found that the ketene imine compound and the ketene compound (1) volatilize during melt mixing. From this, it can be estimated that a part of the imide compound (1) is reacted by heat to form the ketene compound (1) and polyester blocked by the terminal amide group.

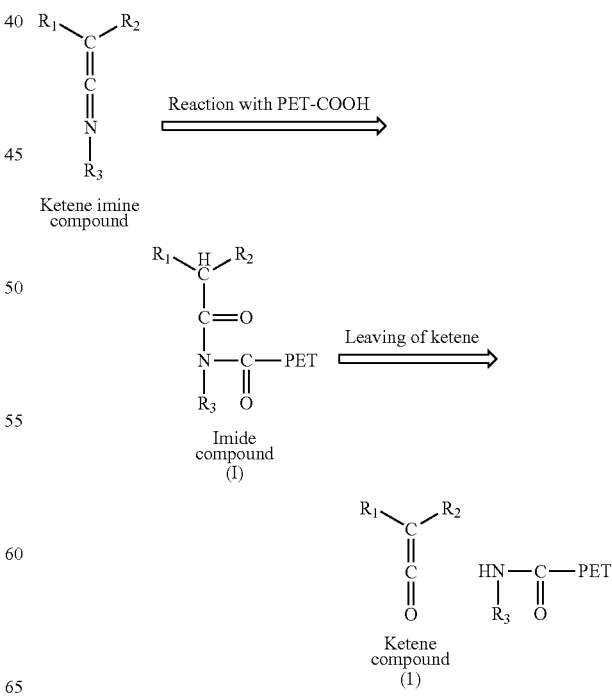

If the ketene imine compound and the ketene compound (1) generated by the above reaction scheme volatilize, the production environment deteriorates, and therefore, this becomes a serious problem.

In contrast, in the chemical modification method of the polyester terminal carboxyl group of the configuration of the present invention, by increasing the molecular weight of the $R_1$—C(=C)—$R_2$ substructure in the ketene imine compound, volatilization of the ketene imine compound itself can be suppressed, and volatilization of the ketene compound produced when blocking the polyester terminal carboxyl group can also be suppressed.

Moreover, in the present invention, by detecting a compound having the $R_1$—C—$R_2$ substructure in the ketene imine compound which is represented by Formula (1) in the molecule from a polyester resin composition or a polyester film, it can be shown that a polyester resin composition including the ketene imine compound which is represented by Formula (1) or a film using the same exists at present or was used in the past. That is, by detecting a compound as the ketene compound (1) from a polyester resin composition or a polyester film, it can be shown that a polyester composition including the ketene imine compound which is represented by Formula (1) was used, and the present invention was performed.

(Polyester Resin Composition)

The polyester resin composition of the present invention includes the above-described ketene imine compound and polyester. Within a range not interfering with the effects of the present invention, various additives, for example, a compatibilizer, a plasticizer, a weathering agent, an antioxidant, a thermal stabilizer, a lubricant, an antistatic agent, a brightener, a colorant, a conductive agent, an ultraviolet absorber, a flame retardant, a flame retardant auxiliary agent, a pigment, a dye, or the like may be included in the polyester resin composition of the present invention.

Although the polyester is not particularly limited, the polyester is preferably saturated polyester. By using such saturated polyester, it is possible to obtain an excellent polyester film compared to the film using unsaturated polyester from the viewpoint of dynamic strength.

The polyester has a —COO— bond or a —OCO— bond in one molecular chain of the polymer. In addition, the terminal group of the polyester is preferably a linear saturated polyester synthesized from an aromatic dibasic acid or an derivative for forming an ester thereof, a diol or an derivative for forming an ester thereof as an OH group, a COOH group, or a protected group thereof (an $OR^X$ group, a $COOR^X$ group ($R^X$ is any substituent such as an alkyl group)). As the linear saturated polyester, for example, those described in JP-A-2009-155479 or JP-A-2010-235824 can be suitably used.

As specific examples of the linear saturated polyester, polyethylene terephthalate (PET), polyethylene isophthalate, polybutylene terephthalate, poly(1,4-cyclohexylenedimethylene terephthalate), polyethylene-2,6-naphthalate, and among these, polyethylene terephthalate or polyethylene-2,6-naphthalate is particularly preferable, and polyethylene terephthalate is more particularly preferable from the viewpoint of the balance between the dynamic properties and the cost. Moreover, whereas a film of polyethylene-2,6-naphthalate or polybutylene terephthalate is produced in a melt state by heating to 230° C. or higher during the film production, a film of PET is produced in a melt state by heating to 270° C. or higher, and thus, a ketene imine compound or a ketene compound is further easily generated, and in the polyester film of the present invention, it is possible to reduce the volatilization amount of the ketene imine compound or the ketene compound even in a case where the polyester is PET.

The polyester may be a homopolymer or a copolymer. Furthermore, it may be a blend of the polyester with a small amount of any other type of resin, for example, polyimide, or the like. In addition, a crystalline polyester which can form anisotropy during film formation in a melt state may be used as the polyester.

For the molecular weight of the polyester, the weight average molecular weight (Mw) is preferably 5000 to 100000, more preferably 8000 to 80000, and particularly preferably 12000 to 60000 from the viewpoint of heat resistance and viscosity. As the weight average molecular weight of the polyester, a value in terms of polymethyl methacrylate (PMMA), measured by gel permeation chromatography (GPC) using hexafluoroisopropanol as a solvent, can be used.

The polyester resin composition of the present invention more preferably includes the ketene imine compound of the present invention of 0.1% by mass to 4% by mass, and particularly preferably includes 0.1% by mass to 2% by mass with respect to the polyester. It is preferable that the polyester resin composition includes the ketene imine compound of the lower limit value or greater from the viewpoint of improving both hydrolysis resistance and film thickness uniformity when forming a polyester film. It is preferable that the polyester resin composition includes the ketene imine compound of the upper limit value or less from the viewpoint of suppressing gelation and improving film thickness uniformity when forming a polyester film.

Here, it may be considered that in order to enhance the hydrolysis resistance of the formed polyester film, it is preferable to block many carboxyl terminals of polyester. However, when putting a large amount of compound such as the ketene imine compound of the present invention into polyester, gel is formed, and the film thickness uniformity of the polyester film is likely to be insufficient. Therefore, it is preferable to control the addition amount of ketene imine compound to be within a specific range. By adjusting the addition amount of ketene imine compound, it is possible to control both hydrolysis resistance and film thickness uniformity of the polyester film to be within a suitable range.

Moreover, the ketene imine compound put in a large amount for a secondary reaction remains as an unreacted ketene imine compound, and further, the unreacted ketene imine compound may be reacted with moisture, the terminal group of polyester, or other free acid, and therefore, it is not preferable.

The polyester resin composition of the present invention does not refuse to include a compound other than the ketene imine compound described above as long as it is not contrary to the spirit of the present invention. For example, the polyester resin composition of the present invention can be used in combination with a carbodiimide compound, an epoxy compound, or an oxazoline compound. The ketene imine compound which is represented by Formula (1) is preferably 70% by mass or greater, more preferably 80% by mass or greater, and particularly preferably 90% by mass or greater with respect to an organic compound other than the polyester included in the polyester resin composition of the present invention.

The polyester can be synthesized according to a known method. For example, polyester can be synthesized according to a known polycondensation method, a ring-opening polymerization method, or the like, which can be applied to any of the reactions by transesterification reaction and direct polymerization.

In a case where the polyester used in the present invention is a polymer or copolymer, obtained by the condensation reaction of an aromatic dibasic acid or an derivative for forming an ester thereof with a diol or an derivative for forming an ester thereof as a main components, the polyester can be produced by subjecting an aromatic dibasic acid or an derivative for forming an ester thereof, and a diol or an derivative for forming an ester thereof to esterification reaction or transesterification reaction, and then to polycondensation reaction. Further, by selecting the raw material or the reaction condition, the carboxylic acid value or the intrinsic viscosity of the polyester can be controlled. Further, in order to perform the esterification or transesterification reaction and the polycondensation reaction effectively, it is preferable to add a polymerization catalyst during these reactions.

As a polymerization catalyst in the polymerization of the polyester, an Al-based, an Sb-based, a Ge-based, or a Ti-based compound is preferably used from the viewpoint of inhibiting the carboxyl group content to a predetermined range or less. Among these, a Ti-based compound is particularly preferable. In the case of using a Ti-based compound, the Ti-based compound is used as the catalyst in the range of the amount of 1 ppm to 30 ppm, and more preferably 3 ppm to 15 ppm to perform polymerization. If the proportion of the Ti-based compound is within the range, it is possible to adjust the terminal carboxyl groups to fall within the range as described below, and it is also possible to keep the hydrolysis resistance of the polymer substrate low.

In the synthesis of the polyester using a Ti-based compound, for example, the methods described in JP-B-8-30119, Japanese Patent Nos. 2543624, 3335683, 3717380, 3897756, 3962226, 3979866, 3996871, 4000867, 4053837, 4127119, 4134710, 4159154, 4269704, 4313538, or the like may be applied.

Preferably, the polyester is one subjected to solid-phase polymerization after polymerization. This can result in the preferable carboxylic acid value. The solid-phase polymerization may be in a continuous method (where the resin is filled in a tower, gradually circulated therein with heating for a predetermined period of time, and then discharged) or in a batch method (where the resin is put into a container and heated therein for a predetermined period of time). Specifically, the methods described in Japanese Patent Nos. 2621563, 3121876, 3136774, 3603585, 3616522, 3617340, 3680523, 3717392, 4167159, or the like may be applied to the solid-phase polymerization.

The temperature of the solid-phase polymerization is preferably 170° C. to 240° C., more preferably 180° C. to 230° C., and still more preferably 190° C. to 220° C. In addition, the time of the solid-phase polymerization is preferably 5 hours to 100 hours, more preferably 10 hours to 75 hours, and still more preferably 15 hours to 50 hours. The solid-phase polymerization is preferably performed in vacuum or in a nitrogen atmosphere.

(Polyester Film)

The present invention relates to a polyester film formed of the polyester resin composition described above.

The thickness of the polyester film of the present invention varies according to the uses, but in a case where polyester film is used as a member of a back sheet for a solar cell module, the thickness is preferably 25 μm to 300 μm, and more preferably 120 μm to 300 μm. When the thickness is 25 μm or greater, a sufficient dynamic strength is obtained, and when the thickness is 300 μm or less, advantage in terms of cost is obtained.

The polyester film of the present invention is preferably stretched, more preferably biaxially stretched, and particularly preferably biaxially stretched in plane compared to stretching of a tubular shape, and more particularly preferably sequentially biaxially stretched. The biaxially stretched polyester film is a film obtained by stretching (hereinafter, referred to as "longitudinal stretching") in the length direction (MD: Machine Direction) and by stretching (hereinafter, referred to as "transverse stretching") in the width direction (TD: Transverse Direction). The longitudinal stretching and the transverse stretching may be performed once, respectively, or may be performed in plural times, and the longitudinal stretching and the transverse stretching may be performed at the same time.

The degree of MD orientation and the degree of TD orientation of the polyester film of the present invention are each preferably 0.14 or greater, more preferably 0.155 or greater, and particularly preferably 0.16 or greater. If each degree of orientation is 0.14 or greater, the restriction of the non-crystalline chain is improved (the mobility is lowered), and the hydrolysis resistance is improved. The degree of MD orientation and the degree of TD orientation can be calculated from the degree of MD orientation: $\Delta n(x-z)$, TD orientation; $\Delta n(y-z)$, by measuring the refractive indices in the x, y, and z directions of the biaxially oriented film at an atmosphere at 25° C., using an Abbe refractometer, a monochromatic light sodium D-line as the light source, and methylene iodine as a mount solution.

The terminal carboxyl group content in the polyester film (the carboxylic acid value of the polyester, hereinafter, referred to as AV) is preferably 25 eq/ton or less, more preferably 20 eq/ton or less, particularly preferably 16 eq/ton or less, and more particularly preferably 15 eq/ton or less with respect to the polyester. If the carboxyl group content is 25 eq/ton or less, the hydrolysis resistance of polyester film and heat resistance by combination with the ketene imine compound are maintained, and thus, reduction of strength at a time of wet heat aging can be suppressed low. The lower limit of the terminal carboxyl group content is desirably 10 eq/ton or greater from the viewpoint of keeping the adhesiveness (adhesive property) among layers (for example, a white layer) formed when the polyester film of the present invention is used as the back sheet for a solar cell module. The terminal carboxyl group content in the polyester can be adjusted by the kind of a polymerization catalyst, the polymerization time, or the film formation conditions (the film formation temperature and time). The carboxyl group content can be measured by a titration method according to the method described in H. A. Pohl, Anal. Chem. 26 (1954) 1614-1616. Specifically, a polyester is dissolved in benzyl alcohol at 205° C. and a phenol red indicator is added. Then, titration is performed with a water/methanol/benzyl alcohol solution of sodium hydroxide, and from the titration amount, the carboxylic acid value (eq/ton) can be calculated.

The terminal hydroxyl group content in the polyester film is preferably 120 eq/ton or less, and more preferably 90 eq/ton or less with respect to the polyester. If the hydroxyl group content is 120 eq/ton or less, the reaction between carbodiimide having a bulky functional group at a specific position described later and the hydroxyl group is suppressed, and thus, the reaction with a carboxyl group is preferentially undergone, which can further reduce the carboxylic acid value. The lower limit of the hydroxyl group content is desirably 20 eq/ton or greater from the viewpoint of adhesiveness with an upper layer. The hydroxyl group content in the polyester can be adjusted by the kind of a polymerization catalyst, the polymerization time, or the film formation conditions (the film formation temperature and time). For the terminal hydroxyl group content, a value measured by $^1$H-NMR, using a deuterated hexafluoroisopropanol solvent, can be used.

In addition, the intrinsic viscosity (IV) of the polyester film of the present invention is preferably 0.70 dl/g to 0.94 dl/g, more preferably 0.71 dl/g to 0.84 dl/g, and particularly preferably 0.72 dl/g to 0.84 dl/g. The intrinsic viscosity of the polyester film is preferably the upper limit value described above or less from the viewpoint of improving film formation properties and the film thickness uniformity.

For the intrinsic viscosity (IV) of polyester, in a case where polyester used during the film production is 2 or more types (for example, a case of using the retrieved polyester of JP-A-2011-256337 or the like), the intrinsic viscosity of polyester obtained by mixing all polyester preferably satisfies the above range.

For the intrinsic viscosity (IV) of polyester, polyester is dissolved in ortho-chlorophenol, and from the solution viscosity measured at 25° C., the intrinsic viscosity can be calculated by the following equation.

$$\eta sp/C = [\eta] + K[\eta]^2 \cdot C$$

Here, $\eta sp$ is (solution viscosity/solvent viscosity)−1, C is the dissolved polymer weight per 100 mL of solvent (1 g/100 mL in this measurement), K is Huggins constant (0.343), and the solution viscosity and the solvent viscosity can be measured using an Ostwald viscometer.

(Production Method of Polyester Film)

(Film Forming Step)

In the film forming step, the melt obtained by meting the polyester and the ketene imine compound included in the resin composition for forming the polyester film of the present invention is passed through a gear pump or a filter, then extruded to a cooling roll through a die, and cooled and solidified, whereby a (unstretched) film can be formed. In this regard, the extruded melt can be adhered to the cooling roll using an electrostatic application method. At this time, the surface temperature of the cooling roll can be usually set to 10° C. to 40° C.

(Stretching Step)

The (unstretched) film formed by the film forming step can be realized by performing a stretching treatment in the stretching step. In the stretching step, a film cooled and solidified (unstretched) by the cooling roller is preferably stretched in one or two directions, and more preferably stretched in two directions. In the stretching in the two directions (biaxial stretching), the longitudinal stretching and the transverse stretching may be performed once, respectively, or may be performed in plural times, and the longitudinal stretching and the transverse stretching may be performed at the same time.

The stretching treatment is performed, preferably at the glass temperature (Tg) ° C. of the film to (Tg+60) ° C., and more preferably Tg+3° C. to Tg+40° C., and more preferably at Tg+5° C. to Tg+30° C.

The preferable stretching ratio is 280% to 500%, more preferably 300% to 480%, and even more preferably 320% to 460% in at least one direction. In the case of biaxial stretching, the stretching may be performed equivalently in the longitudinal and the transverse directions, but it is more preferable that the stretching ratio in one direction is larger than that in the other direction, thereby performing inequivalent stretching. Any one of the longitudinal direction (MD) and the transverse direction (TD) may be larger than the other. The stretching ratio as mentioned herein is determined using the following equation.

Stretching ratio (%)=100×(Length after stretching)/(Length before stretching)

The biaxial stretching treatment is a stretching, for example, at the glass transition temperature $(Tg_1)°$ C. of a film to $(Tg_1+60)°$ C. in the length direction once or two or more times, in which the total ratio is 3- to 6-times and the ratio in the width direction at $(Tg_1)°$ C. to $(Tg+60)°$ C. is 3- to 5-times.

The biaxial stretching treatment can be performed by stretching in the length direction, using two or more pairs of nip rolls that have a higher peripheral speed at an outlet (longitudinal stretching), and can also performed by gripping both ends of the film with chucks and extending them in the perpendicular direction (the direction perpendicular to the length direction) (transverse stretching).

In the stretching step, before the stretching treatment or after the stretching treatment, and preferably after stretching treatment, the film can be subjected to a heat treatment. By performing the heat treatment, fine crystals can be produced, thereby improving the dynamic characteristics or durability. The film can also be subjected to a heat treatment at about 180° C. to 210° C. (more preferably at 185° C. to 220° C.) for 1 second to 60 seconds (more preferably for 2 seconds to 30 seconds).

In the stretching step, the thermal relaxation treatment can be performed after the heat treatment. The thermal relaxation treatment is a treatment for shrinking the film by applying heat to the film for stress relaxation. The thermal relaxation treatment is preferably performed in both directions of MD and TD of the film. For the conditions in the thermal relaxation treatment, the treatment is preferably performed at a temperature lower than the heat treatment temperature, and more preferably at 130° C. to 220° C. In addition, for the thermal relaxation treatment, the thermal shrinkage (150° C.) of the film in both of the MD and the TD is preferably 1% to 12%, and more preferably 1% to 10%. The thermal shrinkage (150° C.) is determined as follows. The thermal shrinkage can be determined from the following formula, by cutting out a sample having a width of 50 mm at 350 mm in the measurement direction, attaching a target point at an interval of 300 mm near the both ends in the length direction of the sample, fixing one end in an oven adjusted to a temperature of 150° C., leaving the other end to be free for 30 minutes, then measuring the distance between the target points at room temperature, taking this length as L (mm), and using this measured values.

150° C. thermal shrinkage (%)=100×(300−L)/300

In addition, a case where the thermal shrinkage is positive denotes shrinkage, and a case where the thermal shrinkage is negative denotes stretching.

As described above, according to the method described above, a film having excellent hydrolysis resistance can be fabricated. The polyester film of the present invention can be appropriately used not only as a protective sheet (back sheet for a solar cell module) for a solar cell module as described below, but also in other applications.

In addition, the film of the present invention can also be used as a laminate including a coating layer containing at least one functional group selected from COOH, OH, $SO_3H$, $NH_2$, and a salt thereof thereon.

(Back Sheet for Solar Cell Module)

The back sheet for a solar cell module of the present invention has the polyester film described above. If the polyester film described above is used for a back sheet for a solar cell module, a problem in adhesiveness among the layers is reduced, and thus, particularly, adhesiveness among the layers after wet heat aging can be greatly improved.

The back sheet for a solar cell module of the present invention may have the following functional layer applied to the polyester film by coating after uniaxial stretching and/or after biaxial stretching. For the application, known coating techniques such as a roll coating method, a knife edge coating method, a gravure coating method, a curtain coating method, and the like can be used.

In addition, a surface treatment (a flame treatment, a corona treatment, a plasma treatment, an ultraviolet treatment, and the like) may also be performed before such the application. Furthermore, bonding using an adhesive is also preferable.

Readily Adhesive Layer

In the back sheet for a solar cell module of the present invention, a readily adhesive layer is preferably provided on the side facing the sealing material of the cell-side substrate, in which a solar cell element is sealed with a sealing material in the case of constituting the solar cell module. By providing a readily adhesive layer exhibiting adhesiveness to an adhered (for example, the surface of the sealing material of the cell-side substrate in which the solar cell element is sealed with the sealing material) including a sealing material (in particular, an ethylene-vinyl acetate copolymer), it is possible to adhere firmly between the back sheet and the sealing material. Specifically, the readily adhesive layer has an adhesion power, in particular with EVA (an ethylene-vinyl acetate copolymer) used as a sealing material, of 10 N/cm or greater, and preferably 20 N/cm or greater.

Furthermore, for the readily adhesive layer, it is required that peeling of the back sheet should not occur during the use of the solar cell module, and thus, it is desirable the readily adhesive layer have high hydrolysis resistance.

A binder, fine particles, a cross-linking agent, an additive, or the like can be contained in the readily adhesive layer. As the binder, the fine particles, the cross-linking agent, the additive, or the like contained in the readily adhesive layer, those described in paragraphs [0142] to [0145] of JP-A-2012-084844 can be used. In addition, regarding the method for forming the readily adhesive layer and the physical properties thereof, the description in paragraphs [0146] and [0147] of JPA-2012-084844 can be referred to.

Colored Layer

The back sheet for a solar cell module of the present invention preferably further has a colored layer. The colored layer is a layer arranged to be in contact with the surface of the polyester film or with another layer interposed therebetween, and can be constituted using a pigment or a binder.

A first function of the colored layer is to increase the power generation efficiency of a solar cell module by reflecting a portion of light in the incident light, which is not used in the power generation at the solar cell and reaches the back sheet, and returning the portion of light to the solar cell. A second function is to enhance the decorative properties of the external appearance when the solar cell module is viewed from the front surface side. Generally, when a solar cell module is viewed from the front surface side, the back sheet is seen around the solar cell. Thus, the decorative properties can be increased by providing a colored layer to the back sheet.

A pigment, a binder, an additive, or the like can be contained in the colored layer. As the pigment, the binder, the additive, or the like contained in the colored layer, those described in paragraphs [0150] to [0157] of JP-A-2012-084844 can be used. In addition, regarding the method for forming the colored layer and the physical properties thereof, the description in paragraphs [0158] to [0160] of JP-A-2012-084844 can be referred to.

Undercoat Layer

The back sheet for a solar cell module of the present invention preferably further has an undercoat layer. For example, when a colored layer is provided, the undercoat layer may be provided between the colored layer and the polyester film. The undercoat layer can be constituted by using a binder, a cross-linking agent, a surfactant, or the like. Regarding the binder or the like contained in the undercoat layer and the method for forming the undercoat layer, the description in paragraphs [0162] to [0164] of JP-A-2012-084844 can be referred to.

Barrier Layer and Antifouling Layer (Fluorine-Based Resin Layer and Silicon-Based Resin Layer)

The back sheet for a solar cell module of the present invention may further have a barrier layer or an antifouling layer. As the barrier layer or the antifouling layer, the barrier layer or the antifouling layer described in paragraphs [0165] to [0173] of JP-A-2012-084844 can be used.

(Solar Cell Module)

The solar cell module of the present invention may have the polyester film of the present invention or the back sheet for a solar cell module of the present invention.

The solar cell module of the present invention is constituted such that a solar cell element that converts the light energy of sunlight to electrical energy is arranged between a transparent substrate, on which sunlight is incident, and the polyester film (back sheet for a solar cell) of the present invention. The space between the substrate and the polyester film can be constituted to be sealed with a resin (a so-called sealing material) such as an ethylene-vinyl acetate copolymer and the like.

The details of the solar cell module, the solar cell, and the members other than the back sheet are described in, for example, "Constituent Materials for Sunlight Power Generation System" (edited by Eiichi Sugimoto, Kogyo Chosakai Publishing Co., Ltd. published in 2008).

The transparent substrate may have light transmitting properties by which sunlight can be transmitted, and can be appropriately selected from base materials that transmit light. From the viewpoint of power generation efficiency, a base material having higher light transmittance is preferable, and as such a substrate, for example, a glass substrate, a substrate of a transparent resin such as an acrylic resin and the like, etc. can be suitably used.

As the solar cell element, various known solar cell elements such as silicon-based elements such as single crystal silicon, polycrystalline silicon, amorphous silicon, and the like; Group III-V or Group II-VI compound semiconductor-based elements such as copper-indium-gallium-selenium, copper-indium-selenium, cadmium-tellurium, gallium-arsenic, and the like; etc. may be applied.

EXAMPLES

Hereinafter, the present invention will be described in more detail with reference to Examples. The materials, use amounts, ratios, processing contents, processing procedures, and the like indicated in the examples below may be changed as appropriate without departing from the gist of the present invention. Therefore, the range of the present invention should not be construed to be limited by the Examples as described below. Unless otherwise specifically indicated, the "part(s)" is on the basis of mass.

Synthesis Example 1

Synthesis of Exemplary Compound 1

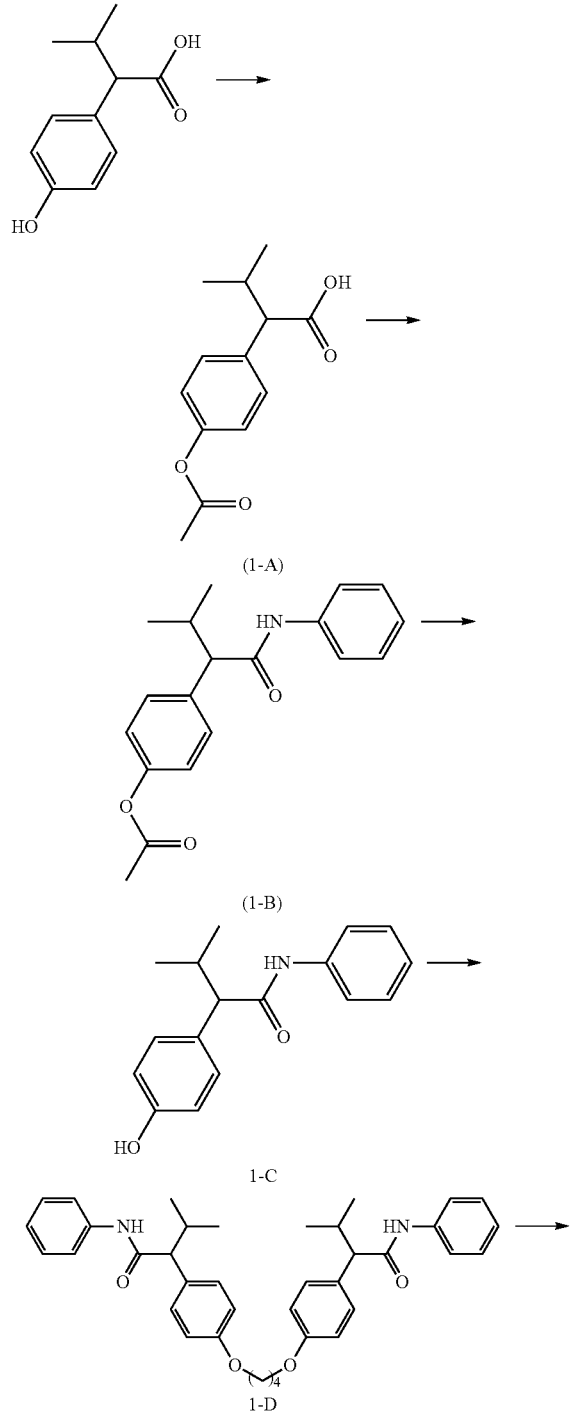

(1-A)

(1-B)

1-C

1-D

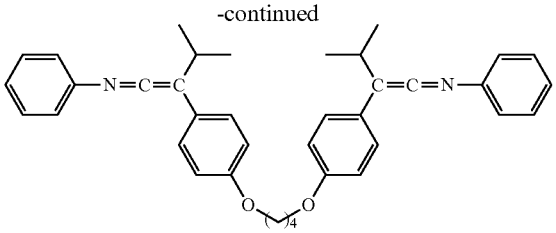

Exemplary Compound (1)

29.1 g (150 mol) of 2-(4-hydroxyphenyl)-3-methylbutyric acid and 375 mL of acetic anhydride were put into a three-necked flask, followed by stirring for 3 hours under reflux. After the completion of the reaction was confirmed by using TLC (thin layer chromatography), the excessive acetic anhydride was distilled off under reduced pressure. The obtained solid was dissolved in ethyl acetate, and liquid-liquid extraction was performed on the resultant product using 1 N hydrochloric acid water. The solvent was distilled off, whereby 31.0 g (yield of 87.5%) of (1-A) was obtained. The structure was confirmed by NMR.

17.1 g (72.4 mmol) of (1-A), 21.5 g (181 mmol) of thionyl chloride, and 50 mL of toluene were put into a three-necked flask, followed by stirring at 70° C. for 1 hour. After the completion of the reaction was confirmed by using TLC, the excessive thionyl chloride and solvent were distilled off under reduced pressure. Next, after 50 mL of toluene was added thereto, the product was dissolved, and cooled to 5° C. 14.8 g (159 mmol) of aniline and 16.1 g (159 mmol) of triethylamine were slowly added dropwise thereto at the same time, followed by stirring for 2 hours under ice-cooling. After the solvent was distilled off under reduced pressure, the resultant product was dissolved in ethyl acetate, and liquid-liquid extraction was performed using 1 N hydrochloric acid water. The solvent was distilled off, whereby 16.2 g of (1-B) was obtained. (Yield of 88%)

16.2 g (52 mmol) of (1-B), 15.0 g of sodium methoxide (28% methanol solution), and 50 mL of methanol were put into a three-necked flask, followed by stirring at room temperature for 2 hours. After the completion of the reaction was confirmed by using TLC, ethyl acetate was added thereto, and liquid-liquid extraction was performed on the resultant product using 1 N hydrochloric acid water. After the solvent was distilled off under reduced pressure, the resultant product was crystallized by using a mixed ethyl acetate/hexane solvent, whereby 12.2 g of (1-C) was obtained. (Yield of 87%)

10.7 g (40 mmol) of (1-C), 16.6 g (120 mmol) of potassium carbonate, and 70 mL of DMF (N,N-dimethylformamide) were put into a three-necked flask, followed by stirring at 50° C. in nitrogen. 4.31 g (20 mmol) of 1,4-dibromobutane was added dropwise thereto, then, the temperature of the system was raised to 110° C., and the mixture was allowed to react for 24 hours. After the reaction, ethyl acetate was added thereto, and liquid-liquid extractions were successively performed on the resultant product using 1 N hydrochloric acid water, 1 N sodium hydrogen carbonate aqueous solution, and then, a saturated sodium chloride aqueous solution. After the solvent was distilled off under reduced pressure, the resultant product was crystallized by using a mixed 2-propanol/hexane solvent, whereby 8.3 g of (1-D) was obtained. (Yield of 70%)

6.0 g (10.1 mmol) of (1-D), 6.9 g (26.3 mmol) of triphenylphosphine, 4.08 g (40.5 mmol) triethylamine, 3.12 g (20.2 mmol) of carbon tetrachloride, and 210 mL of chloroform were put into a three-necked flask, followed by stirring at 70° C. for 8 hours in nitrogen. After the solvent was concentrated under reduced pressure, the resultant product was washed with hexane, and purified by silica gel chromatography, whereby 2.5 g of Exemplary Compound (1) was obtained. (Yield: 45%)

$^1$H-NMR (DMSO-d6) δ (ppm); 1.2 (12H), 1.8-1.9 (4H), 2.9 (2H), 4.0 (4H), 6.9-7.0 (4H), 7.1 (4H), 7.2-7.5 (10H)

Synthesis Example 2

Synthesis of Exemplary Compound 4

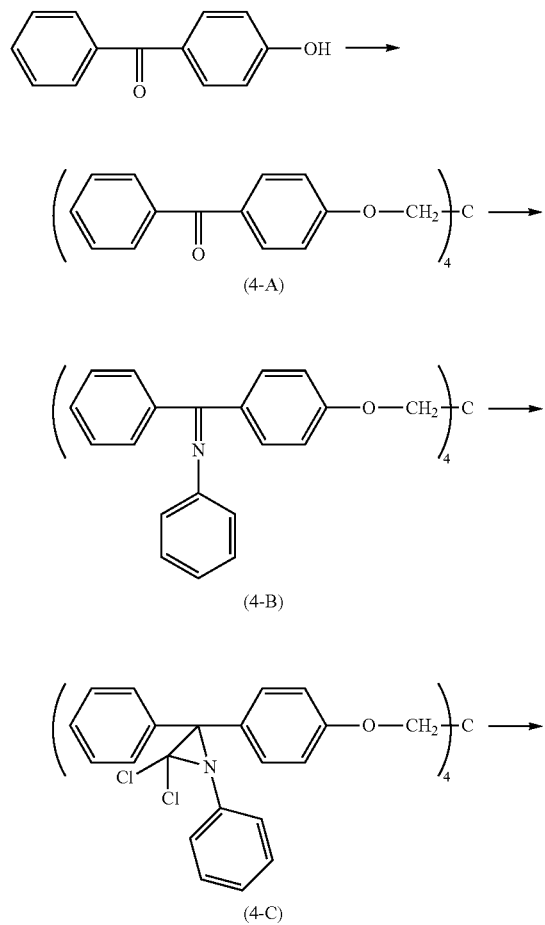

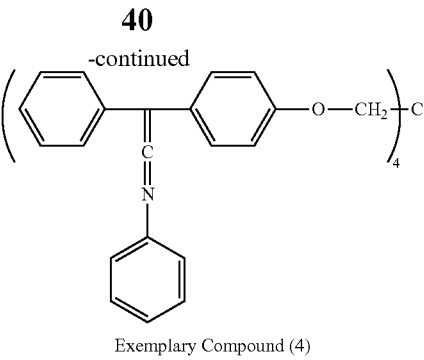

Exemplary Compound (4)

15.1 g (76 mmol) of benzophenone, 6.08 g (16 mmol) of pentaerythritol tetrabromide, 31.1 g (225 mmol) of potassium carbonate, and 130 mL of DMF were put into a three-necked flask, followed by stirring at 130° C. for 10 hours. The solid obtained by distilling off the solvent under reduced pressure was washed once with distilled water and once with ethanol, and then, was crystallized by using ethyl acetate, whereby 13.0 g of (4-A) was obtained (yield of 95%). The structure was confirmed by NMR.

10.9 g (12.7 mmol) of (4-A), 7.08 g (76.2 mmol) of aniline, 22.96 g (154.6 mmol) of DABCO (diazabicyclooctane), and 390 mL of chlorobenzene were put into a three-necked flask, followed by stirring at 125° C. for 1 hour, and then, 9.9 g (51 mmol) of tetrachlorotitanium was added thereto, followed by stirring for 4 hours. The obtained reaction liquid was filtered under reduced pressure and concentrated, and the obtained solid was washed with ethanol, whereby 13.5 g of (4-B) was obtained (yield of 92%). The structure was confirmed by NMR.

10.2 g (8.7 mmol) of (4-B), 6.0 g of triethylbenzylammonium chloride, and 90 mL of chloroform were put into a three-necked flask, and while thoroughly stirring, 60 g of a 50% sodium hydroxide aqueous solution was added thereto at once, followed by stirring at 40° C. to 45° C. for 1 hour. 120 mL of pure water and 180 mL of chloroform were added thereto, then, the resultant product was washed with pure water two times, and the solvent was distilled off under reduced pressure, whereby 12.9 g (8.7 mmol) of (4-C) was obtained (yield of 100%). The structure was confirmed by NMR.

12.9 g (8.7 mmol) of (4-C), 39 g of sodium iodide, and 210 mL of acetone were put into a flask, followed by refluxing at 75° C. for 2 hours. The reaction solution was slowly added dropwise to a 3.5% sodium thiosulfate aqueous solution, then, the resultant product was stirred for 1 hour, and filtered under reduced pressure, whereby a solid was obtained. The obtained solid was purified by column chromatography, whereby 7.2 g (6.0 mmol) of Exemplary Compound (4) was obtained (yield of 69%). The structure was confirmed by NMR.

$^1$H-NMR (CDCl$_3$) δ (ppm); 4.32 (8H), 7.05 (8H), 7.20 (20H), 7.36 (20H), 7.45 (8H)

Synthesis Example 3

Synthesis of Exemplary Compound 7

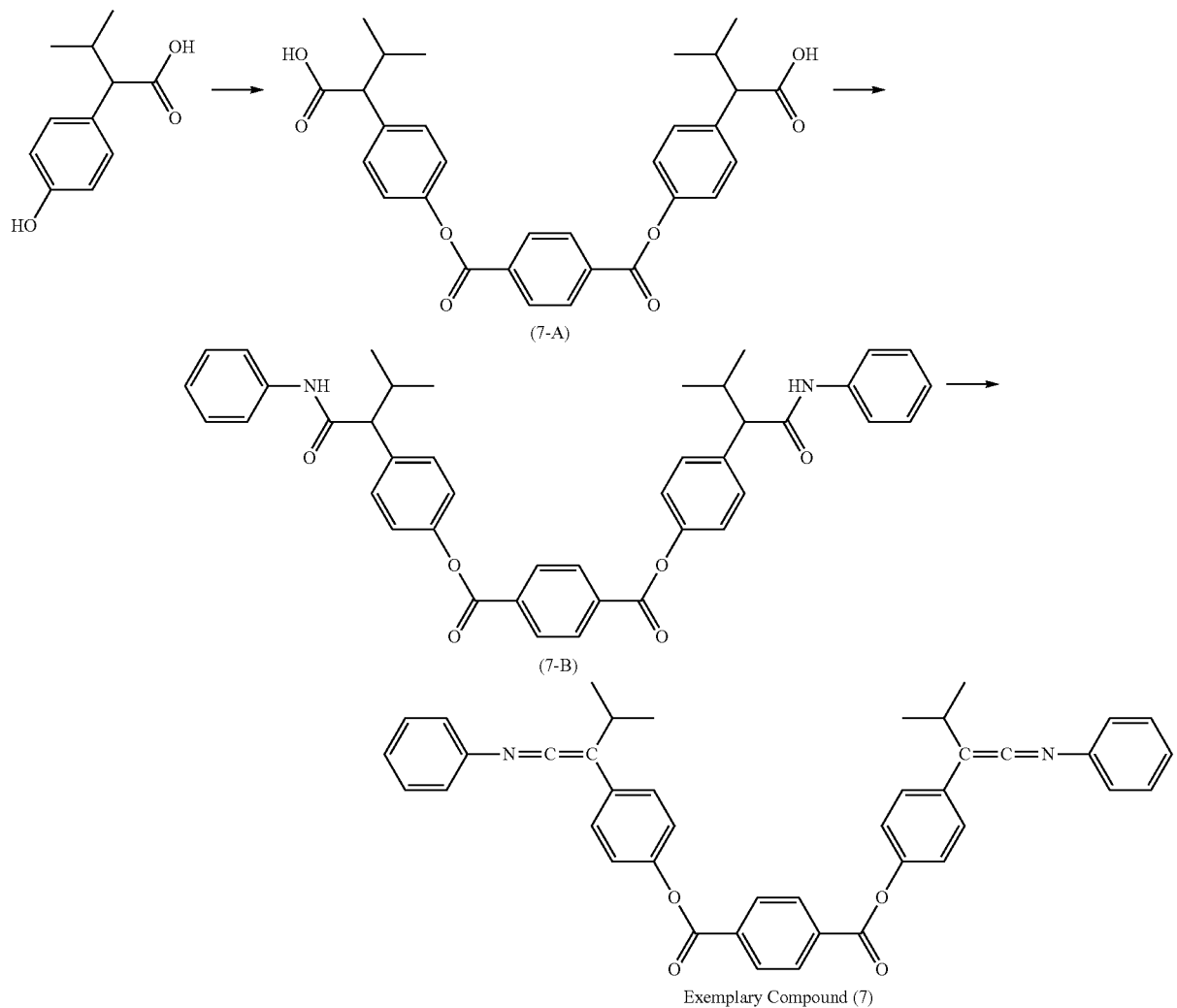

Exemplary Compound (7)

32.0 g (165 mmol) of 2-(4-hydroxyphenyl)-3-methylbutyric acid and 450 mL of a 1 N sodium hydroxide aqueous solution were put into a three-necked flask, followed by stirring at room temperature. A solution of 16.9 g (83 mmol) of terephthaloyl chloride in 100 mL of toluene was added dropwise thereto at room temperature. After the dropping ended, 450 mL of a 2 N sodium hydroxide aqueous solution was added thereto. After being allowed to react for 4 hours, the pH of the system was adjusted to 2 by adding 450 mL of 3 N hydrochloric acid water, whereby a solid was precipitated. The organic layer was filtered, whereby 39.0 g of (7-A) was obtained. (Yield of 88%)

16.0 g (30 mmol) of (7-A) and 180 mL of THF were put into a three-necked flask, and while stirring under ice water, 4.61 mL (30 mmol) of methanesulfonyl chloride was added dropwise thereto, and then, 11.5 mL (66 mmol) of N,N-diisopropylethylamine was added dropwise. After stirring for 5 hours, the completion of the reaction was confirmed using TLC, a solution of 5.04 g (54 mmol) of aniline in 50 mL of THF was added dropwise thereto, then, 11.5 mL (66 mmol) of N,N-diisopropylethylamine was added dropwise, and a small amount of N,N-dimethyl-4-aminopyridine was added thereto. After stirring at room temperature for 3 hours, the completion of the reaction was confirmed using TLC, and liquid-liquid extractions were successively performed on the resultant product using a saturated sodium chloride aqueous solution, 1 N hydrochloric acid water, a saturated sodium chloride aqueous solution, and then, water. After the solvent was distilled off, recrystallization was performed by using ethyl acetate, whereby 11.7 g of (7-B) was obtained. (Yield of 60%)

5.73 g (9.1 mmol) of (7-B), 6.18 g (23.7 mmol) of triphenylphosphine, 3.68 g (36.4 mmol) of triethylamine, 2.80 g (18.2 mmol) of carbon tetrachloride, and 190 mL of chloroform were put into a three-necked flask, followed by stirring at 70° C. for 8 hours in nitrogen. After the solvent was concentrated under reduced pressure, the resultant product was washed with hexane, whereby 3.7 g of Exemplary Compound (7) was obtained. (Yield of 83%)

$^1$H-NMR (DMSO-d6) δ (ppm); 0.6 (6H), 0.9 (6H), 2.1-2.3 (m, 2H), 6.7 (4H), 6.9 (2H), 7.0-7.2 (4H), 7.2-7.3 (4H), 7.3-7.4 (4H), 7.7 (4H)

Synthesis Example 4

Synthesis of Exemplary Compound 9

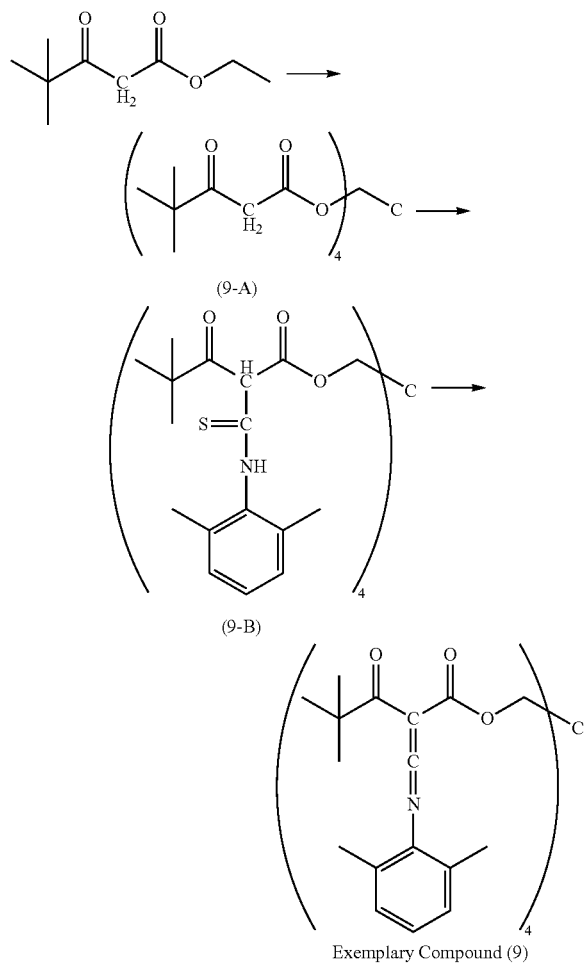

A mixture of 17.2 g (0.1 mol) of ethyl pivaloylacetoacetate, 2.7 g (20 mmol) of pentaerythritol, and 0.3 g (1.5 mmol) of para-toluenesulfonic acid was stirred at 180° C. in a nitrogen atmosphere. After the disappearance of the raw material was confirmed by using TLC, the temperature of the system was lowered to room temperature, and the mixture was dissolved in ethyl acetate. After liquid-liquid separation was performed by adding water, the organic layer was dried over magnesium sulfate, and the solvent was distilled off under reduced pressure. The resultant product was purified by column chromatography, whereby 9.7 g of (9-A) was obtained. (Yield of 76%)

A solution of 10.1 g (62 mmol) of 2,6-dimethyl-phenyl thioisocyanate in 10 mL of tetrahydrofuran was slowly added dropwise to a solution of 9.0 g (14 mmol) of (9-A) and 9.2 mL (62 mmol) of 1,8-diazabicyclo[5.4.0]undec-7-ene in 30 mL of tetrahydrofuran under ice-cooling. After the temperature of the reaction system was raised to room temperature, the disappearance of the raw material was confirmed by using TLC, and liquid-liquid separation was performed by adding water/ethyl acetate. The organic layer was washed with a saline solution, and then, water, and dried over magnesium sulfate. The solvent was distilled off under reduced pressure, and the resultant product was purified by column chromatography, whereby 16.5 g of (9-B) was obtained. (Yield of 91%)

A solution of 2.0 g (11.8 mmol) of 2-chloro-1,3-dimethylimidazolium chloride in 50 mL of chloroform was added to a solution of 10.0 g (7.7 mmol) of (9-B) in 100 mL of chloroform under ice-cooling, and 4.3 mL (30.8 mmol) of triethylamine was slowly added thereto. After the dropping ended, the temperature of the reaction system was slowly raised to room temperature while stirring. After the disappearance of the raw material was confirmed by using TLC, liquid-liquid separation was performed by adding chloroform/water, and the solvent was distilled off under reduced pressure. The resultant product was purified by silica gel column chromatography, whereby 5.6 g of Exemplary Compound (9) was obtained. (Yield of 63%)

$^1$H-NMR (CDCl$_3$-d) δ (ppm); 1.3 (36H), 2.1 (24H), 4.2 (8H), 7.0-7.2 (12H)

Synthesis Example 5

Synthesis of Exemplary Compound 11

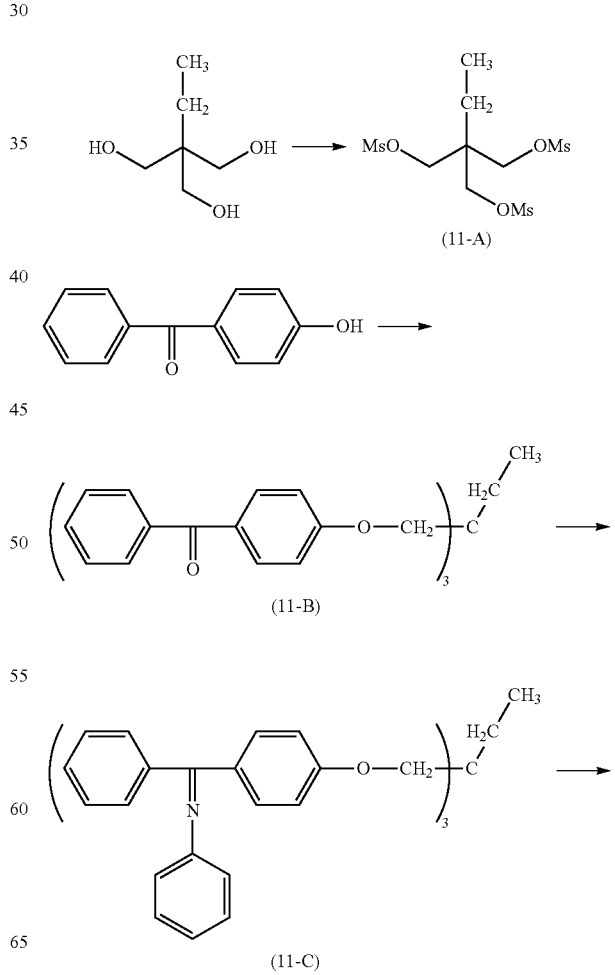

45

-continued

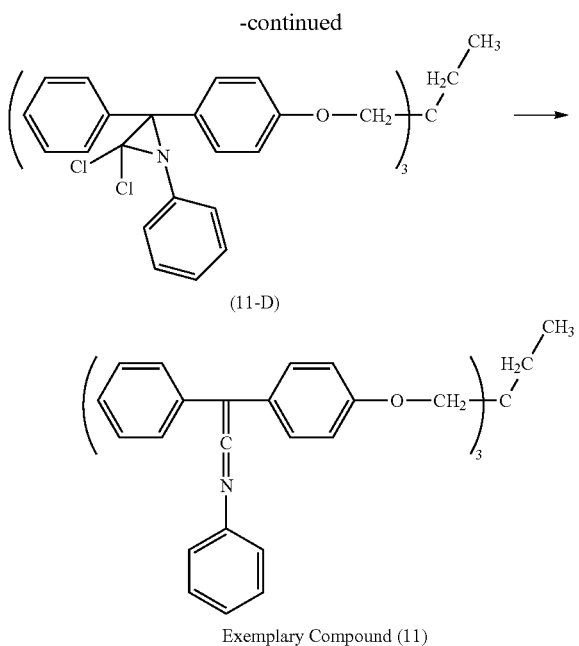

Exemplary Compound (11)

24.0 g (246.2 mmol) of triethylamine was added dropwise to a solution of 10.0 g (74.6 mmol) of trimethylolpropane and 28.2 g (246.2 mmol) of methanesulfonyl chloride in 90 mL of ethyl acetate under ice-cooling. Then, the temperature was raised to room temperature, followed by stirring for 3 hours. After 50 mL of water was added to the reaction system, the resultant product was stirred for 1 hour, whereby crystals were precipitated. The obtained crystals were filtered, and dried, whereby 20.2 g of (11-A) was obtained. (Yield of 74%)

15.1 g (76 mmol) of benzophenone, 7.7 g (21 mmol) of (11-A), 31.5 g (228 mmol) of potassium carbonate, and 130 mL of DMAc were put into a three-necked flask, followed by stirring at 130° C. for 10 hours. After the reaction system was cooled to room temperature, liquid-liquid separation was performed by adding ethyl acetate/water, the aqueous layer was washed with water until the aqueous layer becomes neutral. After the organic layer was dried over magnesium sulfate, the solvent was distilled off under reduced pressure. The resultant product was purified by silica gel column chromatography using a mixed ethyl acetate/hexane solvent, whereby 11 g of (11-B) was obtained. (yield of 78%)

10 g (14.8 mmol) of (11-B), 6.2 g (66.7 mmol) of aniline, 15 g (133.5 mmol) of DABCO (diazabicyclooctane), and 380 mL of chlorobenzene were put into a three-necked flask, followed by stirring at 125° C. for 1 hour, and then, 8.4 g (44.5 mmol) of tetrachlorotitanium was added thereto, followed by stirring for 4 hours. The obtained reaction liquid was filtered under reduced pressure and concentrated, and the obtained solid was washed with ethanol, whereby 12.6 g of (11-C) was obtained. (Yield of 95%) The structure was confirmed by NMR.

4.1 g (4.6 mmol) of (11-C), 2.4 g of triethylbenzylammonium chloride, and 37 mL of chloroform were put into a three-necked flask, and while thoroughly stirring, 24.2 g of a 50% sodium hydroxide aqueous solution was added thereto at once, followed by stirring at 40° C. to 45° C. for 1 hour. 48 mL of pure water and 72 mL of chloroform were added thereto, then, the resultant product was washed with pure water two times, and the solvent was distilled off under reduced pressure, whereby 5.2 g (4.6 mmol) of (11-D) was obtained. (Yield of 100%) The structure was confirmed by NMR.

5.2 g (4.6 mmol) of (11-D), 20 g (136.8 mmol) of sodium iodide, and 100 mL of acetone were put into a flask, followed by refluxing at 75° C. for 2 hours. The reaction solution was slowly added dropwise to a 3.5% sodium thiosulfate aqueous solution, then, the resultant product was stirred for 1 hour, and filtered under reduced pressure, whereby a solid was obtained. The obtained solid was purified by column chromatography, whereby 2.8 g of Exemplary Compound (11) was obtained. (Yield of 65%) The structure was confirmed by NMR.

$^1$H-NMR (CDCl$_3$) δ (ppm); 1.0 (3H), 1.8 (2H), 3.9 (6H), 7.1 (6H), 7.2 (15H), 7.4 (15H), 7.5 (6H)

Synthesis Example 6

Synthesis of Exemplary Compound 17

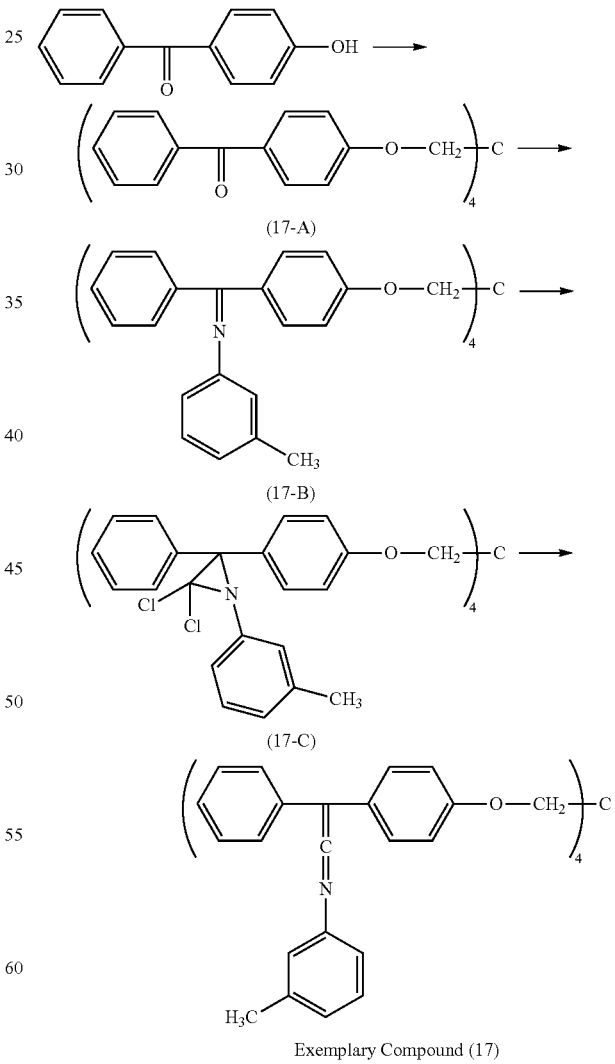

Exemplary Compound (17)

Exemplary Compound (17) was obtained in the same operation as in Synthesis Example 2 except that metatoluidine was used instead of aniline of Exemplary Compound (4) in Synthesis Example 2.

Synthesis Example 7

Synthesis of Exemplary Compound 18

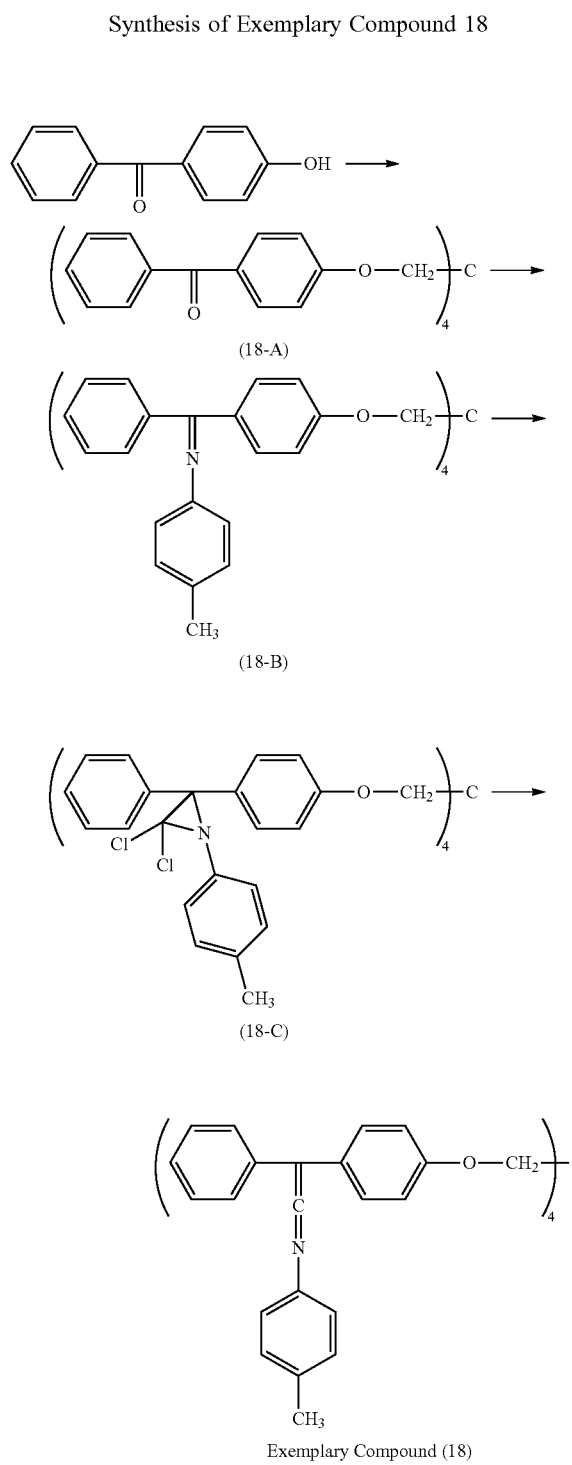

Exemplary Compound (18)

Exemplary Compound (18) was obtained in the same operation as in Synthesis Example 2 except that para-toluidine was used instead of aniline of Exemplary Compound (4) in Synthesis Example 2.

Synthesis Example 8

Synthesis of Exemplary Compound 19

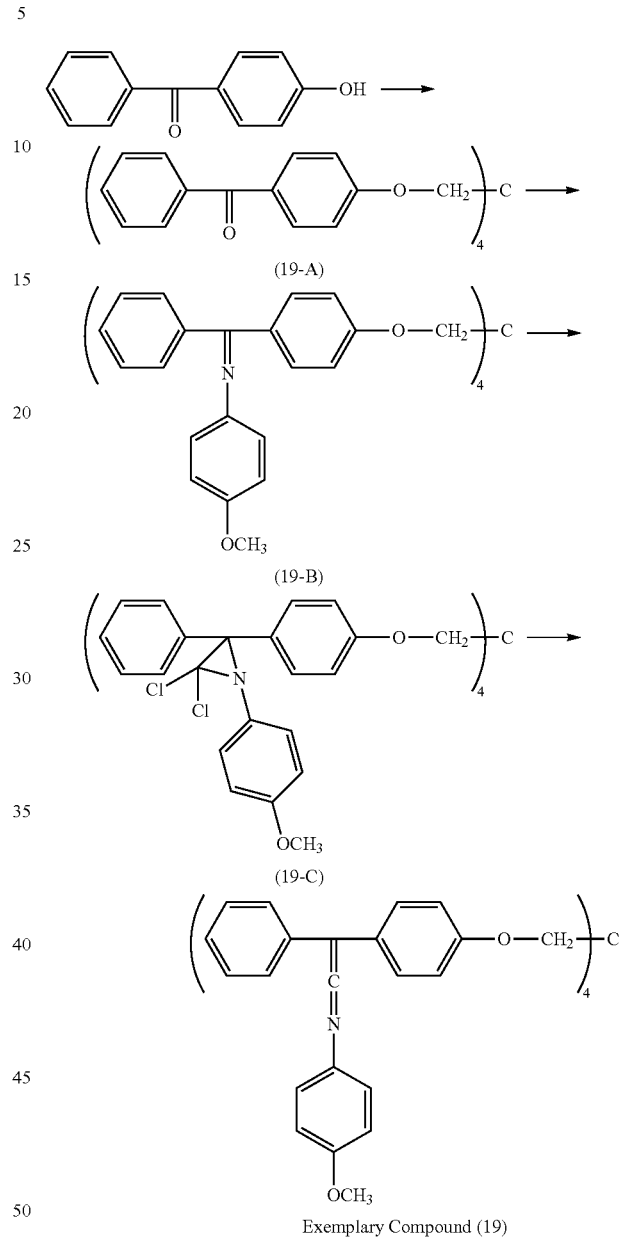

Exemplary Compound (19)

Exemplary Compound (19) was obtained in the same operation as in Synthesis Example 2 except that para-anisidine was used instead of aniline of Exemplary Compound (4) in Synthesis Example 2.

Synthesis Example 9

Synthesis of Exemplary Compound 20

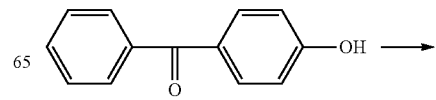

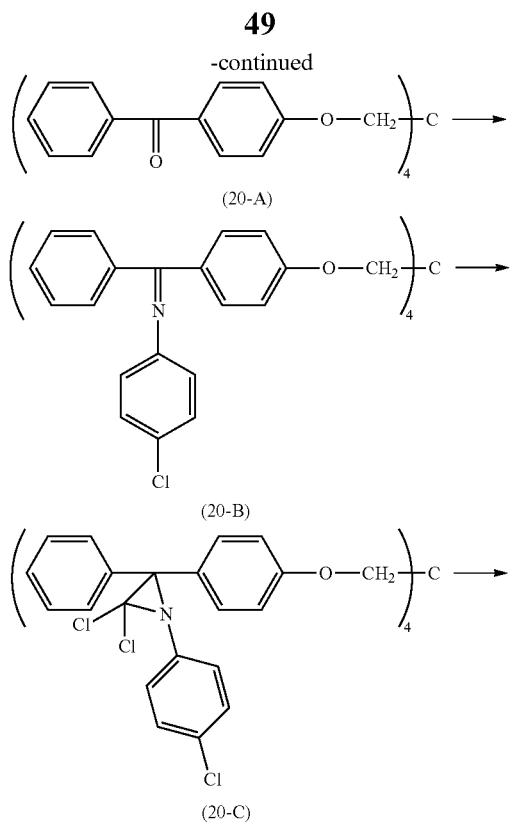
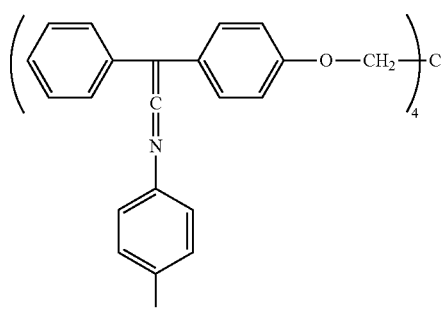
Exemplary Compound (20)
Exemplary Compound (20) was obtained in the same operation as in Synthesis Example 2 except that para-chloroaniline was used instead of aniline of Exemplary Compound (4) in Synthesis Example 2.
Synthesis Example 10
Synthesis of Exemplary Compound 37
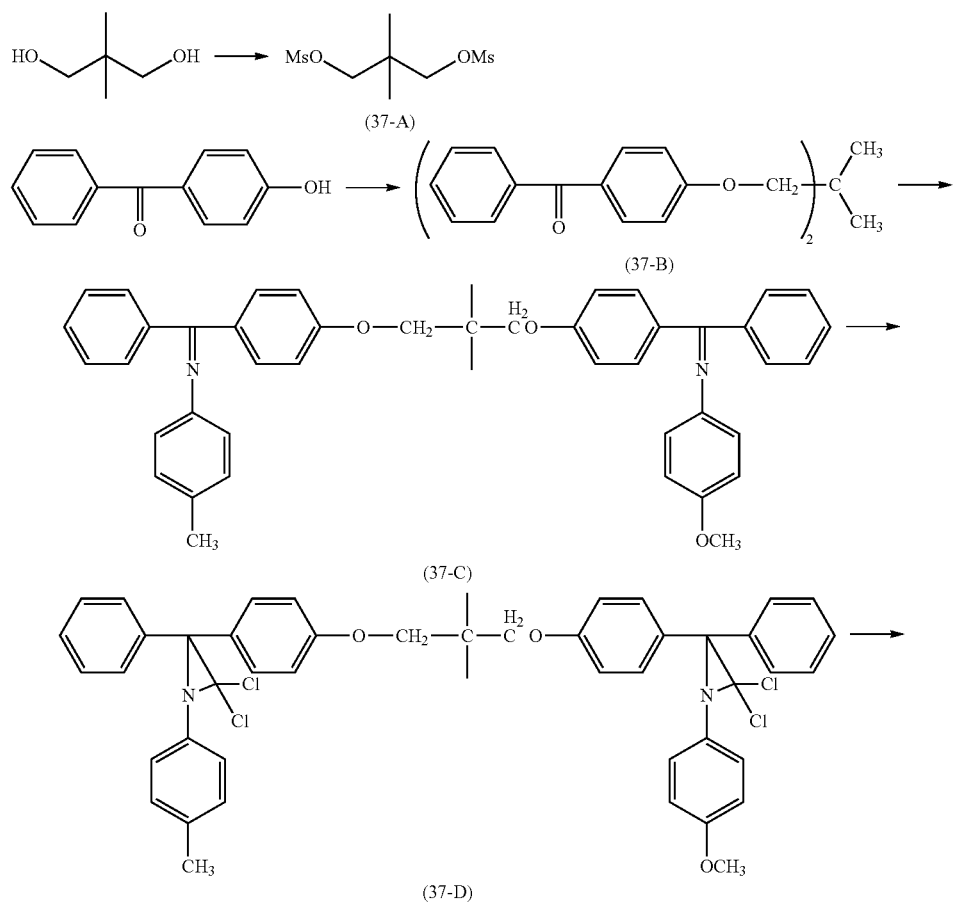

-continued

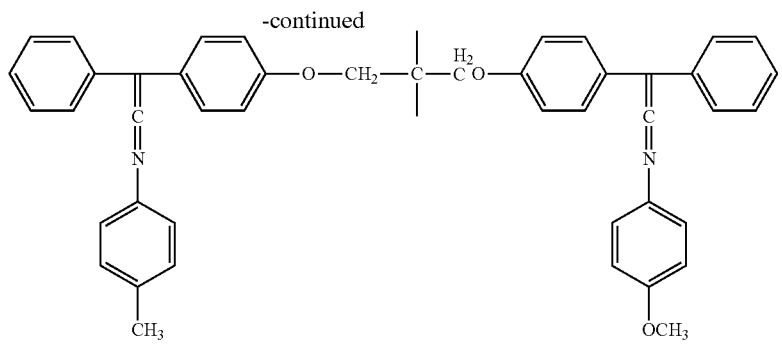

Exemplary Compound (37)

21.4 g (211.2 mmol) of triethylamine was added dropwise to a solution of 10.0 g (96 mmol) of neopentyl glycol and 24.2 g (211.2 mmol) of methanesulfonyl chloride in 90 mL of ethyl acetate under ice-cooling. Then, the temperature was raised to room temperature, followed by stirring for 3 hours. After 50 mL of water was added to the reaction system, the resultant product was stirred for 1 hour, and liquid-liquid separation was performed. After the organic layer was dried over magnesium sulfate, the solvent was distilled off under reduced pressure, whereby 25 g of (37-A) was obtained. (Yield of quant.)

14.7 g (74 mmol) of benzophenone, 8.1 g (31 mmol) of (37-A), 30.8 g (223 mmol) of potassium carbonate, and 130 mL of DMAc were put into a three-necked flask, followed by stirring at 130° C. for 18 hours. After the reaction system was cooled to room temperature, liquid-liquid separation was performed by adding ethyl acetate/water, the aqueous layer was washed with water until the aqueous layer becomes neutral. After the organic layer was dried over magnesium sulfate, the solvent was distilled off under reduced pressure. By crystallization from ethanol, 9 g of (37-B) was obtained. (Yield of 63%)

8.2 g (17.7 mmol) of (37-B), 3.3 g (27 mmol) of para-anisidine, 2.9 g (27 mmol) of para-toluidine, 12 g (106 mmol) of DABCO (diazabicyclooctane), and 300 mL of chlorobenzene were put into a three-necked flask, followed by stirring at 125° C. for 1 hour, and then, 6.7 g (35.3 mmol) of tetrachlorotitanium was added thereto, followed by stirring for 4 hours. The obtained reaction liquid was filtered under reduced pressure, and concentrated. The resultant product was purified by silica gel column chromatography using a mixed chloroform/methanol solvent as an eluent, whereby 8.5 g of (37-C) was obtained. (Yield of 73%) The structure was confirmed by NMR.

9.4 g (14.3 mmol) of (37-C), 0.4 g of triethylbenzylammonium chloride, and 60 mL of chloroform were put into a three-necked flask, and while thoroughly stirring, 40 g of a 50% sodium hydroxide aqueous solution was added thereto at once, followed by stirring at 40° C. to 45° C. for 1 hour. 80 mL of pure water and 120 mL of chloroform were added thereto, then, the resultant product was washed with pure water two times, and the solvent was distilled off under reduced pressure, whereby 11.8 g (14.3 mmol) of (37-D) was obtained. (Yield of 100%) The structure was confirmed by NMR.

11.8 g (14.3 mmol) of (13-D), 42.9 g (286 mmol) of sodium iodide, and 220 mL of acetone were put into a flask, followed by refluxing at 75° C. for 2 hours. The reaction solution was slowly added dropwise to a 3.5% sodium thiosulfate aqueous solution, then, the resultant product was stirred for 1 hour, and filtered under reduced pressure, whereby a solid was obtained. The obtained solid was purified by column chromatography, whereby 6.9 g of Exemplary Compound (37) was obtained. (Yield of 71%)

As a ketene imine-based terminal blocking agent, the following compounds were used in each Comparative Example. The ketene imine compounds of Comparative Example 1 (molecular weight of 269) and Comparative Example 2 (molecular weight of 550) are the compounds referred to as "mono" and "bis" in Example of U.S. Pat. No. 3,692,745. Moreover, the molecular weight of the portion corresponding to the $R_1$—C(=C)—$R_2$ substructure in Formula (1) in Comparative Compound 1 or Comparative Compound 2 is 178, respectively.

Comparative Compound 1

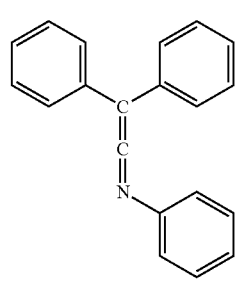

Mw269

Comparative Compound 2

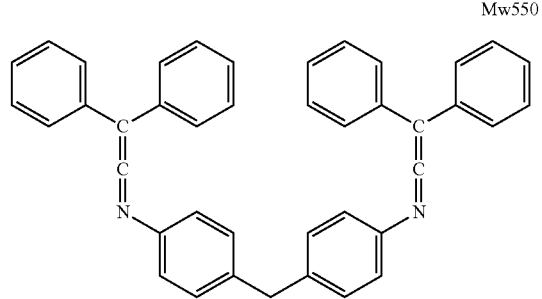

Mw550

Example 1

1. Preparation of Saturated Polyester Resin

Step (A)

4.7 tons of high-purity terephthalic acid and 1.8 tons of ethylene glycol were mixed over 90 minutes to form slurry, and the slurry was continuously supplied to a first esterification reaction tank at a flow rate of 3800 kg/h. Subsequently, an ethylene glycol solution of a citric acid chelated titanium complex ("VERTEC AC-420", manufactured by Johnson Matthey Plc.) having Ti metal coordinated with citric acid was continuously supplied to a first esterification reaction tank and a reaction was performed at a temperature inside the reaction tank of 250° C. and for an average retention time of about 4.4 hours with stirring, thereby obtaining an oligomer. At this time, the citric acid chelated titanium complex was continuously added such that the addition amount of Ti was 9 ppm in terms of elements. The acid value of the obtained oligomer was 500 eq/ton.

The obtained oligomer was transferred to a second esterification reaction tank, and with stirring, the reaction product was allowed to react at a temperature inside the reaction tank of 250° C. for an average retention time of 1.2 hours to obtain an oligomer having an acid value of 180 eq/ton. The inside of the second esterification reaction tank was divided into three zones ranging a first zone to a third zone. At a second zone, an ethylene glycol solution of magnesium acetate was continuously supplied in a manner that the addition amount of Mg was 75 ppm in terms of elements. After that, at a third zone, an ethylene glycol solution of trimethyl phosphate was continuously supplied in a manner that the addition amount of P was 65 ppm in terms of elements. Moreover, the ethylene glycol solution of trimethyl phosphate was prepared by adding a trimethyl phosphate solution at 25° C. to an ethylene glycol solution at 25° C., followed by stirring at 25° C. for 2 hours (content of phosphorous compounds in the solution: 3.8% by mass).

Thus, an esterification reaction product was obtained.

Step (B)

The esterification reaction product obtained in the step (A) was continuously supplied to a first polycondensation reaction tank. Subsequently, polycondensation (transesterification reaction) was performed with stirring the esterification reaction product at a reaction temperature of 270° C. and a pressure inside the reaction tank of 20 torr ($2.67 \times 10^{-3}$ MPa) for an average retention time of about 1.8 hours.

Then, the obtained reaction product was transferred from the first polycondensation reaction tank to a second polycondensation reaction tank, and in the second polycondensation reaction tank, a reaction (transesterification reaction) was performed with stirring under the conditions of a temperature inside the reaction tank of 276° C. and a pressure inside the reaction tank of 5 torr ($6.67 \times 10^{-4}$ MPa) for a retention time of about 1.2 hours.

Subsequently, the reaction product obtained by the transesterification reaction was transferred from the second polycondensation reaction tank to a third polycondensation reaction tank, and in this reaction tank, a reaction (transesterification reaction) was performed with stirring under the conditions of a temperature inside the reaction tank of 276° C. and a pressure inside the reaction tank of 1.5 torr ($2.0 \times 10^{-4}$ MPa) for a retention time of 1.5 hours to obtain a reaction product (polyethylene terephthalate (PET)) having a carboxylic acid value of 22 eq/ton and an IV (intrinsic viscosity) of 0.65 dl/g.

Furthermore, the obtained PET was subjected to a heat treatment (solid-phase polymerization) at 205° C. for 24 hours under a nitrogen gas flow using a continuous solid-phase polymerizer. Moreover, by increasing the solid-phase polymerization time, IV is easily increased and AV is easily reduced, and by increasing the solid-phase polymerization temperature, the AV is easily increased and the IV is easily reduced.

Thereafter, nitrogen gas of 25° C. is flowed into the vacuum polymerizer, and a pellet was cooled to 25° C., whereby PET having a carboxylic acid value of 15 eq/ton and an IV of 0.78 dl/g was obtained.

2. Fabrication of Polyester Film and Evaluation

Extrusion-Molding (Synthesis Step/Film Forming Step)

The obtained PET was put into a hopper of twin-screw kneading extruder having a diameter of 50 mm using a main feeder, and Exemplary Compound (1) of the present invention was put into a subfeeder, and melting and extrusion were performed at 280° C. The extruded melt was passed through a gear pump and a filter (pore diameter of 20 μm), and extruded from a die to a cooling roll at 20° C., whereby an amorphous sheet was obtained. Moreover, the extruded melt was adhered to the cooling roll using an electrostatic application method.

Stretching (Biaxial Stretching Step)

An unstretched film which extruded onto the cooling roll and solidified was subjected to sequential biaxial stretching by the following method, whereby a polyester film having a thickness of 175 μm was obtained.

<Stretching Method>

(a) Longitudinal Stretching

The unstretched film is passed through between two pairs of nip rolls having different peripheral speed, and by this, the unstretched film was stretched in the longitudinal direction (transport direction). Moreover, the stretching was performed at a preheating temperature of 90° C., a stretching temperature of 90° C., a stretching ratio of 3.5 times, and a stretching speed of 3000%/sec.

(b) Transverse Stretching

The longitudinally stretched film was transversely stretched under the following conditions using a tenter.

<Conditions>

Preheating temperature: 100° C.
Stretching temperature: 110° C.
Stretching ratio: 4.2 times
Stretching speed: 70%/sec Heat Fixing and Thermal Relaxation Subsequently, the stretched film after finishing the longitudinal stretching and transverse stretching was heat-fixed under the following conditions. Furthermore, after heat fixing, the tenter width was shorten and thermal relaxation was performed under the following conditions.

<Heat Fixing Conditions>

Heat fixing temperature: 198° C.
Heat fixing time: 2 seconds

<Thermal Relaxation Conditions>

Thermal relaxation temperature: 195° C.
Thermal relaxation ratio: 5%

Winding

After the heat fixing and the thermal relaxation, both ends of the polyester film were trimmed by 10 cm. Thereafter, after knurling 10 mm width of both ends, the polyester film was wound up at a tension of 25 kg/m. Moreover, the width was 1.5 m, and the winding length was 2000 m.

In the above manner, the polyester film of Example 1 was produced. The obtained sample film has a good surface state in which there is no pit or wrinkle.

Process Evaluation (Gas)

Sensory evaluation of the smoke and the smell generated from a die of a twin-screw extruder was performed, and the volatilization was evaluated based on the following criteria. The obtained results are shown in the following Table 1.

<Criteria>

A: There was no occurrence of smoke and smell.

B: There was no occurrence of smoke but there was occurrence of smell.

C: There was occurrence of smoke and smell.

Performance of Polyester Film (Wet Heat Resistance (PCT Test))

Hydrolysis resistance was evaluated by a half-life period of a retention rate of tensile elongation at break. The half-life period of a retention rate of tensile elongation at break was evaluated by subjecting the polyester film obtained in Example 1 to a storage treatment (heat treatment) under the conditions of 120° C. and relative humidity of 100% and measuring the storage time when tensile elongation at break (%) shown by the polyester film after storage becomes 50% of tensile elongation at break (%) shown by the polyester film before storage. The obtained results are shown in Table 1 below.

A: The half-life period of tensile elongation at break was 160 hours or greater

B: The half-life period of tensile elongation at break was 130 hours or greater and less than 160 hours C: The half-life period of tensile elongation at break was less than 130 hours.

It shows that as the half-life period of a retention rate of tensile elongation at break is longer, the hydrolysis resistance of the polyester film is excellent. That is, in the polyester film of the present invention, the half-life period of tensile elongation at break before and after the storage treatment under the conditions of 120° C. and relative humidity of 100% is preferably 130 hours or greater, and more preferably 160 hours or greater.

(Volatile Component)

For the obtained polyester film, the amount of volatile components in the film based on the following criteria was measured by gas chromatography (trade name P&T-GC/MS, manufactured by JASCO Corporation), and evaluation was performed according to the following criteria. Moreover, a compound derived from ketene imine is included in the volatile components, and specifically, a ketene imine compound and a ketene compound are included. That is, a small detected amount of the volatile components means that volatilization of the ketene imine compound and the ketene compound is small, and manufacturing environment is improved. The obtained results are shown in the following Table 1.

<Conditions>

The obtained polyester film was heated at 280° C. for 10 minutes, and generated gas was detected.

<Criteria>

A: A compound derived from ketene imine was under the detection limit.

B: A compound derived from ketene imine was slightly detected.

C: A compound derived from ketene imine was detected.

3. Fabrication of Back Sheet for Solar Cell Module

A back sheet for a solar cell module was fabricated, using the polyester film produced in Example 1.

First, on one surface of the polyester film produced in Example 1, the following (i) reflective layer and (ii) readily adhesive layer were applied in this order by coating.

(i) Reflective Layer (Colored Layer)

All the components having the following composition were mixed and subjected to a dispersion treatment for 1 hour with a dyno-mill disperser, thereby preparing a pigment dispersion.

<Formulation of Pigment Dispersion>

| | |
|---|---|
| Titanium dioxide (TIPAQUE R-780-2, manufactured by Ishihara Sangyo Kaisha, Ltd., 100% by mass of solid content) | 39.9 parts |
| Polyvinyl alcohol (PVA-105, manufactured by Kuraray Co., Ltd., 10% of solid content) | 8.0 parts |
| Surfactant (DEMOL EP, manufactured by Kao Corp., 25% of solid content) | 0.5 parts |
| Distilled water | 51.6 parts |

Then, using the obtained pigment dispersion, all of the components having the following composition were mixed to prepare a coating liquid for forming a reflective layer.

<Formulation of Coating Liquid for Forming Reflective Layer>

| | |
|---|---|
| Pigment dispersion described above | 71.4 parts |
| Polyacrylic resin water dispersion (binder: JURYMER ET410, manufactured by Nihon Junyaku Co., Ltd., 30% by mass of solid content) | 17.1 parts |
| Polyoxyalkylene alkyl ether (NAROACTY CL95, manufactured by Sanyo Chemical Industries, Ltd., 1% by mass of solid content) | 2.7 parts |
| Oxazoline compound (cross-linking agent) (EPOCROS WS-700, manufactured by NIPPON SHOKUBAI Co., Ltd., 25% by mass of solid content) | 1.8 parts |
| Distilled water | 7.0 parts |

The coating liquid for forming a reflective layer obtained above was coated on the polyester film of Example 1 by a bar coater, and dried at 180° C. for 1 minute, thereby forming a (i) reflective layer (white layer) having a titanium dioxide coating amount of 6.5 g/m$^2$.

(ii) Readily Adhesive Layer

All of the components with the following composition were mixed to prepare a coating liquid for a readily adhesive layer. The coating liquid was coated onto the (i) reflective layer such that the binder coating amount becomes 0.09 g/m$^2$, and then dried at 180° C. for 1 minute to form (ii) a readily adhesive layer.

<Composition of Coating Liquid for Forming Readily Adhesive Layer>

| | |
|---|---|
| Polyolefin resin water dispersion (carboxylic acid-containing binder: CHEMIPEARL S75N, manufactured by Mitsui chemicals, Inc., 24% by mass of solid content) | 5.2 parts |
| Polyoxyalkylene alkyl ether (NAROACTY CL95, manufactured by Sanyo Chemical Industries, Ltd., 1% by mass of solid content) | 7.8 parts |
| Oxazoline compound (EPOCROS WS-700, manufactured by NIPPON SHOKUBAI Co., Ltd., 25% by mass of solid content) | 0.8 parts |
| Silica fine particle water dispersion (AEROSIL OX-50, manufactured by Nippon Aerosil Co., Ltd., 10% by mass of solid content) | 2.9 parts |
| Distilled water | 83.3 parts |

Next, on the surface side opposite to the side having (i) the reflective layer and (ii) the readily adhesive layer of the polyester film formed thereon, the following (iii) undercoat layer, (iv) barrier layer, and (v) antifouling layer were applied by coating successively from the polyester film side.

(iii) Undercoat Layer

All of the components with the following composition were mixed to prepare a coating liquid for forming an undercoat layer. This coating liquid was coated on the polyester film and dried at 180° C. for one minute to form an undercoat layer (dried coating amount: about 0.1 g/m$^2$).

<Composition of Coating Liquid for Forming Undercoat Layer>

| | |
|---|---|
| Polyester resin (VYLONAL MD-1200, manufactured by TOYOBO Co., Ltd., 17% by mass of solid content) | 1.7 parts |
| Polyester resin (sulfonic acid-containing binder: PESRESIN A-520, manufactured by TAKAMATSU OIL&FAT Co., Ltd., 30% by mass of solid content) | 3.8 parts |
| Polyoxyalkylene alkyl ether (NAROACTY CL95, manufactured by Sanyo Chemical Industries, Ltd., 1% by mass of solid content) | 1.5 parts |
| Carbodiimide compound (CARBODILITE V-02-L2, manufactured by Nisshinbo Industries, Inc., 10% by mass of solid content) | 1.3 parts |
| Distilled water | 91.7 parts |

(iv) Barrier Layer

Subsequently, on the surface of thus formed undercoat layer, an 800 angstroms thick vacuum deposition film of silicon oxide was formed under the following vacuum deposition conditions. The film served as a barrier layer.

<Vacuum Deposition Conditions> reactive gas mixing ratio (unit: slm): hexamethyl disiloxane/oxygen gas/helium=1/10/10

Vacuum degree inside vacuum chamber: $5.0 \times 10^{-6}$ mbar

Vacuum degree inside deposition chamber: $6.0 \times 10^{-2}$ mbar

Electric power supplied to cooling and electrode drums: 20 kW

Film conveying speed: 80 m/min (v) Antifouling Layer

As shown below, coating liquids for forming a first antifouling layer and a second antifouling layer were prepared. The coating liquid for forming the first antifouling layer and the coating liquid for forming the second antifouling layer were coated in this order on the barrier layer, so that an antifouling layer having a bi-layer structure was applied by coating.

<First Antifouling Layer>

Preparation of Coating Liquid for Forming First Antifouling Layer

The components with the following composition were mixed to prepare a coating liquid for forming the first antifouling layer.

<Composition of Coating Liquid>

| | |
|---|---|
| CERANATE WSA1070 (manufactured by DIC Corp.) | 45.9 parts |
| Oxazoline compound (cross-linking agent) (EPOCROS WS-700, manufactured by NIPPON SHOKUBAI Co., Ltd., 25% by mass of solid content) | 7.7 parts |
| Polyoxyalkylene alkyl ether (NAROACTY CL95, manufactured by Sanyo Chemical Industries, Ltd., 1% by mass of solid content) | 2.0 parts |
| Pigment dispersion used for the reflective layer | 33.0 parts |
| Distilled water | 11.4 parts |

Formation of First Antifouling Layer

The obtained coating liquid was coated on the barrier layer to a binder coating amount of 3.0 g/m$^2$, and dried at 180° C. for 1 minute to form the first antifouling layer.

Preparation of Coating Liquid for Forming Second Antifouling Layer

The components with the following composition were mixed to prepare a coating liquid for forming the second antifouling layer.

<Composition of Coating Liquid>

| | |
|---|---|
| Fluorobinder: Obbligato (manufactured by AGC Coat-tech) | 45.9 parts |
| Oxazoline compound (EPOCROS WS-700, manufactured by NIPPON SHOKUBAI Co., Ltd., 25% by mass of solid content; cross-linking agent) | 7.7 parts |
| Polyoxyalkylene alkyl ether (NAROACTY CL95, manufactured by Sanyo Chemical Industries, Ltd., 1% by mass of solid content) | 2.0 parts |
| Pigment dispersion prepared for the reflective layer | 33.0 parts |
| Distilled water | 11.4 parts |

Formation of Second Antifouling Layer

The prepared coating liquid for forming the second antifouling layer was coated on the first antifouling layer formed on the barrier layer such that the binder coating amount becomes 2.0 g/m$^2$, and dried at 180° C. for 1 minute to form the second antifouling layer.

As described above, the back sheet for a solar cell module of Example 1, which has a reflective layer and readily adhesive layer on one side of the polyester film, and has an undercoat layer, a barrier layer, and an antifouling layer on the other side, was fabricated.

Examples 2 to 13 and Comparative Examples 1 to 2

A polyester film of each of Examples and Comparative Examples was produced in the same manner as in Example 1 except that the ketene imine compound described in the following Table 1 and the amount thereof are changed.

In the same manner as in Example 1 except for using the obtained polyester film of each of Examples and Comparative Examples, a back sheet for a solar cell module of each of Examples and Comparative Examples was fabricated.

In each of Examples and Comparative Examples, the results of evaluation performed in the same manner as in Example 1 are shown in Table 1 below.

TABLE 1

| | Ketene imine compound | | Molecular weight (Mw) of the portion corresponding to $R_1$—C(=C)—$R_2$ substructure | Production adaptability Volatilization of gas | Performance of polyester film | |
|---|---|---|---|---|---|---|
| | Type | Amount [with respect to polyester] | | | Wet heat resistance | Volatile component |
| Example 1 | Exemplary Compound (1) | 0.4 parts by mass | 374 | A | A | A |
| Example 2 | Exemplary Compound (1) | 1.0 part by mass | 374 | A | A | A |
| Example 3 | Exemplary Compound (1) | 2.0 parts by mass | 374 | A | A | A |
| Example 4 | Exemplary Compound (4) | 0.4 parts by mass | 840 | A | A | A |
| Example 5 | Exemplary Compound (4) | 1.0 part by mass | 840 | A | A | A |
| Example 6 | Exemplary Compound (4) | 2.0 parts by mass | 840 | A | A | A |
| Example 7 | Exemplary Compound (7) | 1.0 part by mass | 450 | A | A | A |
| Example 8 | Exemplary Compound (9) | 1.0 part by mass | 680 | A | A | A |
| Example 9 | Exemplary Compound (11) | 1.0 part by mass | 893 | A | A | A |
| Example 10 | Exemplary Compound (17) | 1.0 part by mass | 840 | A | A | A |
| Example 11 | Exemplary Compound (18) | 1.0 part by mass | 840 | A | A | A |
| Example 12 | Exemplary Compound (19) | 1.0 part by mass | 840 | A | A | A |
| Example 13 | Exemplary Compound (20) | 1.0 part by mass | 840 | A | A | A |
| Example 13 | Exemplary Compound (37) | 1.0 part by mass | 456 | A | A | A |
| Comparative Example 1 | Comparative Compound (1) | 1.0 part by mass | 178 | C | A | C |
| Comparative Example 1 | Comparative Compound (2) | 1.0 part by mass | 178 | B | A | B |

From the above Table 1, it was found that generation of gas when using ketene imine compounds which are represented by Formula (1) of the present invention used in each Example could be suppressed, the obtained polyester film of each Example was excellent in hydrolysis resistance, and the content of volatile components in the film was small.

Moreover, the present invention is not limited to exhibit the following effects, and the polyester film of each Example was also good in wet heat resistance.

[Fabrication of Solar Cell]

The back sheet for a solar cell module of each Example fabricated as described above was bonded to a transparent filler to form the structure as in FIG. 1 in JP-A-2009-158952, thereby fabricating a solar cell module. At this time, adhesion was made such that the readily adhesive layer of the back sheet for a solar cell module of each Example was in contact with the transparent filler in which solar cell elements were embedded.

It was confirmed that the fabricated solar cell module can generate power stably over a long period of time.

INDUSTRIAL APPLICABILITY

According to the present invention, it is possible to suppress volatilization of the ketene imine compound or the ketene compound when forming a polyester film. Thus, it is possible to obtain a polyester film having excellent hydrolysis resistance, and the polyester film has high industrial applicability.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/079840, filed Nov. 5, 2013, and Japanese Patent Application No. 2012-244742 filed on Nov. 6, 2012, and Japanese Patent Application No. 2013-228466 filed on Nov. 1, 2013, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. A polyester resin composition including a monoketene imine compound represented by the following Formula (1) and polyester;

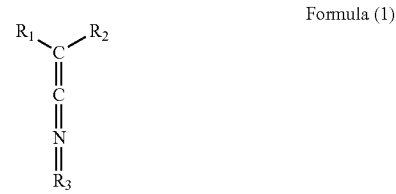

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 400 or greater; and $R_3$ represents an alkyl group which may have a substituent or an aryl group which may have a substituent.

2. A polyester resin composition including a ketene imine compound represented by the following Formula (2) and polyester;

Formula (2)

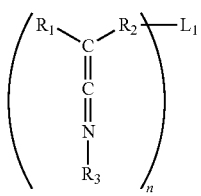

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent; $R_3$ represents an alkyl group which may have a substituent or an aryl group which may have a substituent; n represents an integer of 3 or 4, and $L_1$ represents an n valent group; and the $(R_1-C(=C)-R_2-)_n-L_1$ substructure has a molecular weight of 320 or greater.

3. A polyester resin composition including a ketene imine compound represented by the following Formula (3) and polyester;

Formula (3)

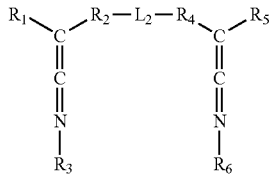

wherein $R_1$ and $R_5$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ and $R_4$ each independently represents an aryl group which has $L_2$ as a substituent; $R_3$ and $R_6$ each independently represents an alkyl group which may have a substituent or an aryl group which may have a substituent; $L_2$ represents a divalent linking group; and the $R_1-C(=C)-R_2-L_2-R_4-C(=C)$13 $R_5$ substructure has a molecular weight of 320 or greater.

4. A ketene imine compound represented by the following Formula (4);

Formula (4)

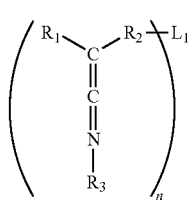

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an aryl group which has $L_1$ as a substituent; $R_3$ represents an alkyl group which may have a substituent or an aryl group which may have a substituent; n represents an integer of 2 to 4, and $L_1$ represents an n valent linking group.

5. The ketene imine compound according to claim 4, wherein the ketene imine compound is represented by the following Formula (5);

Formula (5)

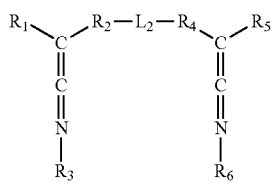

wherein $R_1$ and $R_5$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ and $R_4$ each independently represents an aryl group which has $L_2$ as a substituent; $R_3$ and $R_6$ each independently represents an alkyl group which may have a substituent or an aryl group which may have a substituent; and $L_2$ represents a divalent linking group.

6. A polyester film formed of a polyester resin composition including a monoketene imine compound represented by the following Formula (1) and polyester;

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 400 or greater; and $R_3$ represents an alkyl group which may have a substituent or an aryl group which may have a substituent.

7. A back sheet for a solar cell module having a polyester film formed of a polyester resin composition including a monoketene imine compound represented by the following general Formula (1) and polyester;

Formula (1)

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 400 or greater; and $R_3$ represents an alkyl group which may have a substituent or an aryl group which may have a substituent.

8. A solar cell module having a back sheet having a polyester film formed of a polyester resin composition including a monoketene imine compound represented by the following general Formula (1) and polyester;

Formula (1)

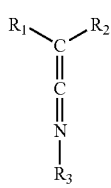

wherein, $R_1$ and $R_2$ each independently represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent, and the $R_1$—C(=C)—$R_2$ substructure has a molecular weight of 400 or greater; and $R_3$ represents an alkyl group which may have a substituent or an aryl group which may have a substituent.

9. A polyester film formed of a polyester resin composition including a ketene imine compound represented by the following Formula (2) and polyester;

Formula (2)

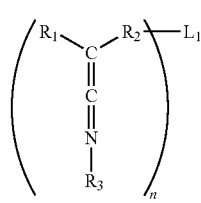

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an aryl group which has $L_1$ as a substituent; $R_3$ represents an alkyl group which may have a substituent or an aryl group which may have a substituent; n represents an integer of 2, and $L_1$ represents an n valent group; and the $(R_1$—C(=C)—$R_2$-$)_n$-$L_1$ substructure has a molecular weight of 320 or greater.

10. A polyester film formed of a polyester resin composition including a ketene imine compound represented by the following Formula (2) and polyester;

Formula (2)

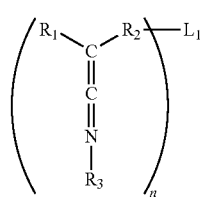

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent; $R_3$ represents an alkyl group which may have a substituent or an aryl group which may have a substituent; n represents an integer of 3 or 4, and $L_1$ represents an n valent group; and the $(R_1-C(=C)-R_2-)_n-L_1$ substructure has a molecular weight of 320 or greater.

11. A back sheet for a solar cell module having a polyester film formed of a polyester resin composition including a ketene imine compound represented by the following general Formula (2) and polyester;

Formula (2)

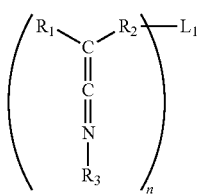

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an aryl group which has $L_1$ as a substituent; $R_3$ represents an alkyl group which may have a substituent or an aryl group which may have a substituent; n represents an integer of 2, and $L_1$ represents an n valent group; and the $(R_1-C(=C)-R_2-)_n-L_1$ substructure has a molecular weight of 320 or greater.

12. A back sheet for a solar cell module having a polyester film formed of a polyester resin composition including a ketene imine compound represented by the following general Formula (2) and polyester;

Formula (2)

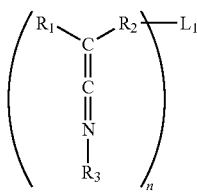

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent; $R_3$ represents an alkyl group which may have a substituent or an aryl group which may have a substituent; n represents an integer of 3 or 4, and $L_1$ represents an n valent group; and the $(R_1-C(=C)-R_2-)_n-L_1$ substructure has a molecular weight of 320 or greater.

13. A solar cell module having a back sheet having a polyester film formed of a polyester resin composition including a ketene imine compound represented by the following general Formula (2) and polyester;

Formula (2)

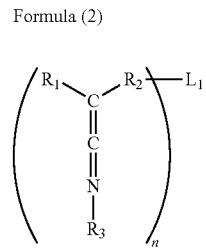

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an aryl group which has $L_1$ as a substituent; $R_3$ represents an alkyl group which may have a substituent or an aryl group which may have a substituent; n represents an integer of 2, and $L_1$ represents an n valent group; and the $(R_1-C(=C)-R_2-)_n-L_1$ substructure has a molecular weight of 320 or greater.

14. A solar cell module having a back sheet having a polyester film formed of a polyester resin composition including a ketene imine compound represented by the following general Formula (2) and polyester;

Formula (2)

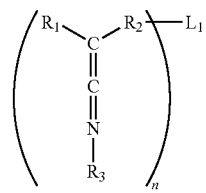

wherein $R_1$ represents an alkyl group which may have a substituent, an aryl group which may have a substituent, an alkoxy group which may have a substituent, an alkoxycarbonyl group which may have a substituent, an aminocarbonyl group which may have a substituent, an aryloxy group which may have a substituent, an acyl group which may have a substituent, or an aryloxycarbonyl group which may have a substituent; $R_2$ represents an alkyl group which has $L_1$ as a substituent, an aryl group which has $L_1$ as a substituent, an alkoxy group which has $L_1$ as a substituent, an alkoxycarbonyl group which has $L_1$ as a substituent, an aminocarbonyl group which has $L_1$ as a substituent, an aryloxy group which has $L_1$ as a substituent, an acyl group which has $L_1$ as a substituent, or an aryloxycarbonyl group which has $L_1$ as a substituent; $R_3$ represents an alkyl group which may have a substituent or an aryl group which may have a substituent; n represents an integer of 3 or 4, and $L_1$ represents an n valent group; and the $(R_1-C(=C)-R_2-)_n-L_1$ substructure has a molecular weight of 320 or greater.

* * * * *